(12) United States Patent
Ohta et al.

(10) Patent No.: US 8,314,396 B2
(45) Date of Patent: Nov. 20, 2012

(54) PORTABLE RADIOGRAPHIC IMAGE CAPTURING DEVICE

(75) Inventors: Yasunori Ohta, Kanagawa (JP); Naoyuki Nishino, Kanagawa (JP); Naoto Iwakiri, Kanagawa (JP); Futoshi Yoshida, Kanagawa (JP); Haruyasu Nakatsugawa, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 106 days.

(21) Appl. No.: 12/890,731

(22) Filed: Sep. 27, 2010

(65) Prior Publication Data

US 2011/0073765 A1    Mar. 31, 2011

(30) Foreign Application Priority Data

Sep. 30, 2009   (JP) ................................ 2009-227865

(51) Int. Cl.
*G01T 1/24* (2006.01)
(52) U.S. Cl. ................................. 250/370.08
(58) Field of Classification Search ............... 250/336.1, 250/361 R, 370.07, 370.08, 370.11
See application file for complete search history.

(56) References Cited

U.S. PATENT DOCUMENTS

| | | | |
|---|---|---|---|
| 7,180,110 B2 * | 2/2007 | Komatsu et al. | 257/291 |
| 2006/0054822 A1 * | 3/2006 | Tsuchino | 250/336.1 |
| 2006/0097177 A1 * | 5/2006 | Yamamoto | 250/370.08 |

FOREIGN PATENT DOCUMENTS

| | | | |
|---|---|---|---|
| JP | 20000010220 A | * | 1/2000 |
| JP | 2002-311526 A | | 10/2002 |
| JP | 2009-32854 A | | 2/2009 |
| JP | 2009-80103 A | | 4/2009 |

\* cited by examiner

*Primary Examiner* — Mark R Gaworecki
(74) *Attorney, Agent, or Firm* — SOLARIS Intellectual Property Group, PLLC

(57) ABSTRACT

A portable radiographic image capturing device has: an image capturing unit at which is provided a radiation surface onto which radiation is irradiated at a time of capturing a radiographic image, and that captures a radiographic image expressed by radiation irradiated onto the radiation surface, and that incorporates therein a radiation detector that outputs electric signals expressing a captured radiographic image; and a control unit that is connected to the image capturing unit, and that incorporates therein a controller that controls image capturing operations of the radiation detector, and that can be changed between an expanded state in which the radiation surface is exposed to an exterior and a housed state in which the control unit covers the radiation surface.

20 Claims, 19 Drawing Sheets

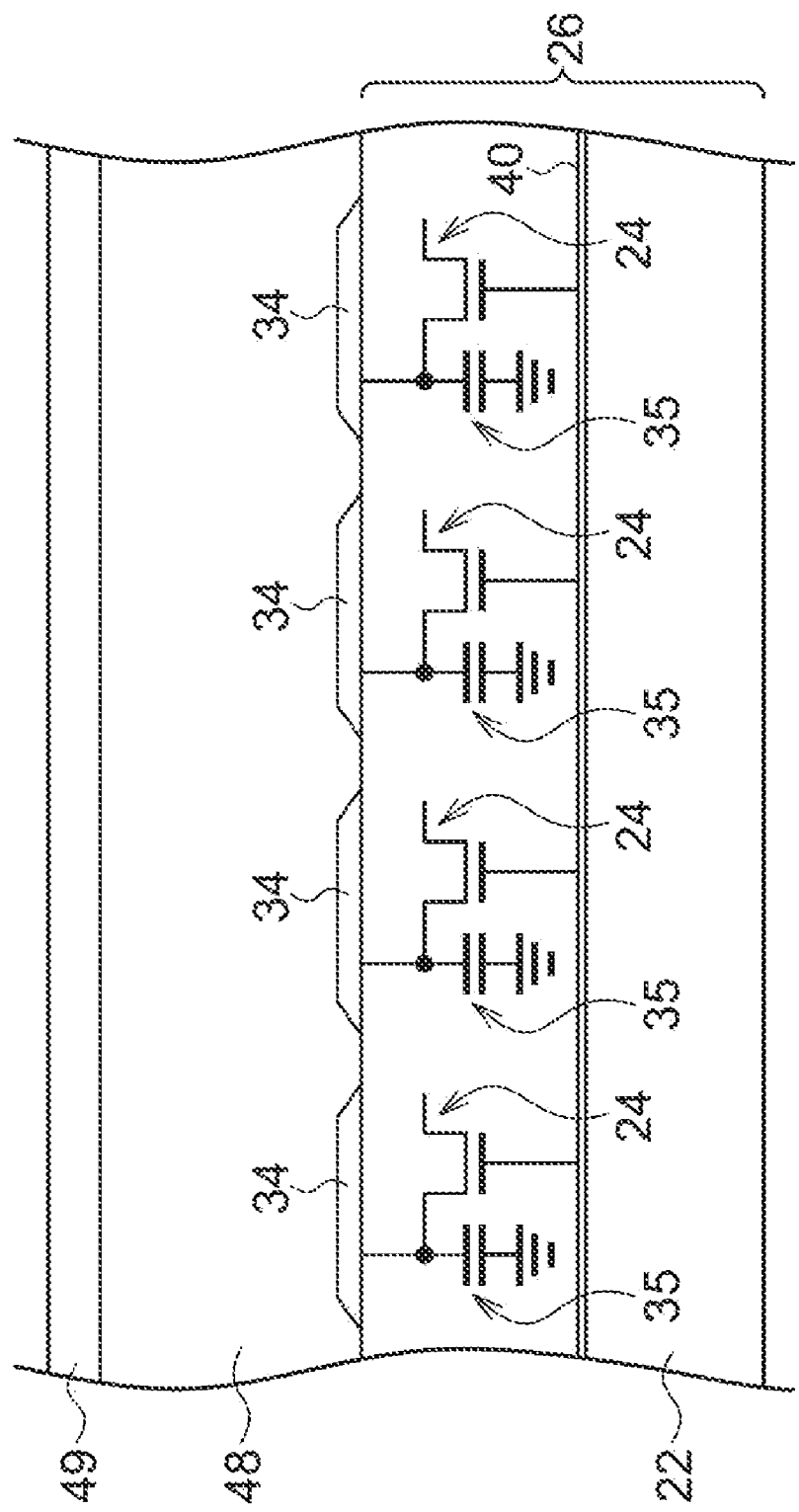

PORTABLE RADIOGRAPHIC IMAGE CAPTURING DEVICE

CROSS-REFERENCE TO RELATED APPLICATION

This application is based on and claims priority under 35 USC 119 from Japanese Patent Application No. 2009-227865 filed on Sep. 30, 2009, the disclosure of which is incorporated by reference herein.

BACKGROUND

1. Technical Field

The present invention relates to a portable radiographic image capturing device that captures a radiographic image expressed by radiation emission.

2. Related Art

Radiation detectors such as FPDs (Flat Panel Detectors), in which a radiation-sensitive layer is disposed on a TFT (Thin Film Transistor) active matrix substrate and that detect irradiated radiation such as X-rays or the like and output electric signals expressing the radiographic image expressed by the detected radiation, and the like have been put into practice in recent years. As compared with a conventional imaging plate, a radiation detector has the advantages that images can be confirmed immediately, and video images also can be confirmed.

Portable radiographic image capturing devices (hereinafter also called electronic cassettes), that incorporate a radiation detector therein and store radiographic image data outputted from the radiation detector, also are being put into practice. Because the electronic cassette has excellent portability, images of a patient can be captured while the patient lies as is on a stretcher or a bed, and it is also easy to adjust the region to be captured by changing the position of the electronic cassette. Therefore, even situations in which images of a patient who cannot move are to be captured can be dealt with flexibly.

It is generally known that the electrical characteristics of a radiation detector change due to a rise in temperature. Further, heat dissipation and cooling are extremely important in order to improve normal operation and durability of the electric parts.

Thus, in Japanese Patent Application Laid-Open (JP-A) No. 2009-80103, the present applicants disclose a technique in which an electronic cassette is structured by a cassette main body that incorporates a radiation detector therein, and a control unit that is freely detachable from and can be separated from the cassette main body, and that supplies electric power to the radiation detector, and that controls the radiation detector and receives image information. The electronic cassette is structured such that electronic parts that generate heat and the radiation detector can be separated.

Further, JP-A No. 2002-311526 discloses a technique in which a portion of a casing of an electronic cassette can be opened and closed, and a unit part, that includes a radiation detector and that is made into a unit, is structured so as to be removable.

By using the technique disclosed in JP-A No. 2009-80103, the control unit is structured so as to be able to be separated from the cassette main body. By using the technique disclosed in JP-A No. 2002-311526, a portion of the casing of the electronic cassette can be opened and closed, and the unit part is structured so as to be removable. The section that generates heat can thereby be separated from the radiation detector.

However, the techniques disclosed in JP-A No. 2009-80103, and JP-A No. 2002-311526 are not techniques that improve the heat dissipating and cooling efficiency of the electronic cassette itself.

Further, generally, a radiation detector is equipped with an image capturing surface onto which the radiation, that has passed through the subject such as a patient or the like, is irradiated, and the radiographic image that is irradiated onto this image capturing surface is captured. Because the image capturing surface is exposed, it is easily damaged. If the image capturing surface is damaged, it affects the captured radiographic image as well.

In particular, because an electronic cassette can be carried about, it is easy for the radiation surface to be damaged while the electronic cassette is being transported.

SUMMARY

In view of the above-described circumstances, the present invention provides a portable radiographic image capturing device that, while improving the cooling effect, can prevent a radiation surface from being damaged when the portable radiographic image capturing device is carried around.

A portable radiographic image capturing device relating to an aspect of the present invention has: an image capturing unit at which is provided a radiation surface that is irradiated at a time of capturing a radiographic image, and that captures a radiographic image expressed by radiation irradiated onto the radiation surface, and that incorporates therein a radiation detector that outputs electric signals expressing a captured radiographic image; and a control unit that is connected to the image capturing unit, and that incorporates therein a controller that controls image capturing operations of the radiation detector, and that can be changed between an expanded state in which the radiation surface is exposed to an exterior and a housed state in which the control unit covers the radiation surface.

In the portable radiographic image capturing device relating to the aspect of the present invention, a radiographic image, that is expressed by radiation irradiated onto the radiation surface, is captured by the image capturing unit at which is provided the radiation surface onto which radiation is irradiated at the time of capturing a radiographic image. The radiation detector, that outputs electric signals expressing the captured radiographic image, is incorporated in the image capturing unit. Radiographic images expressed by radiation that is irradiated onto the radiation surface can be captured. Further, a controller, that controls the image capturing operations of the radiation detector, is incorporated in the control unit that is connected to the image capturing unit. The control unit can be changed between the expanded state in which the radiation surface is exposed to the exterior and the housed state in which the control unit covers the radiation surface.

BRIEF DESCRIPTION OF THE DRAWINGS

Exemplary embodiments of the present invention will be described in detail based on the following figures, wherein:

FIG. 19 is a sectional view schematically showing the structure of a direct-conversion-type radiation detector relating to another exemplary embodiment.

DETAILED DESCRIPTION

First Exemplary Embodiment

Figure 1:
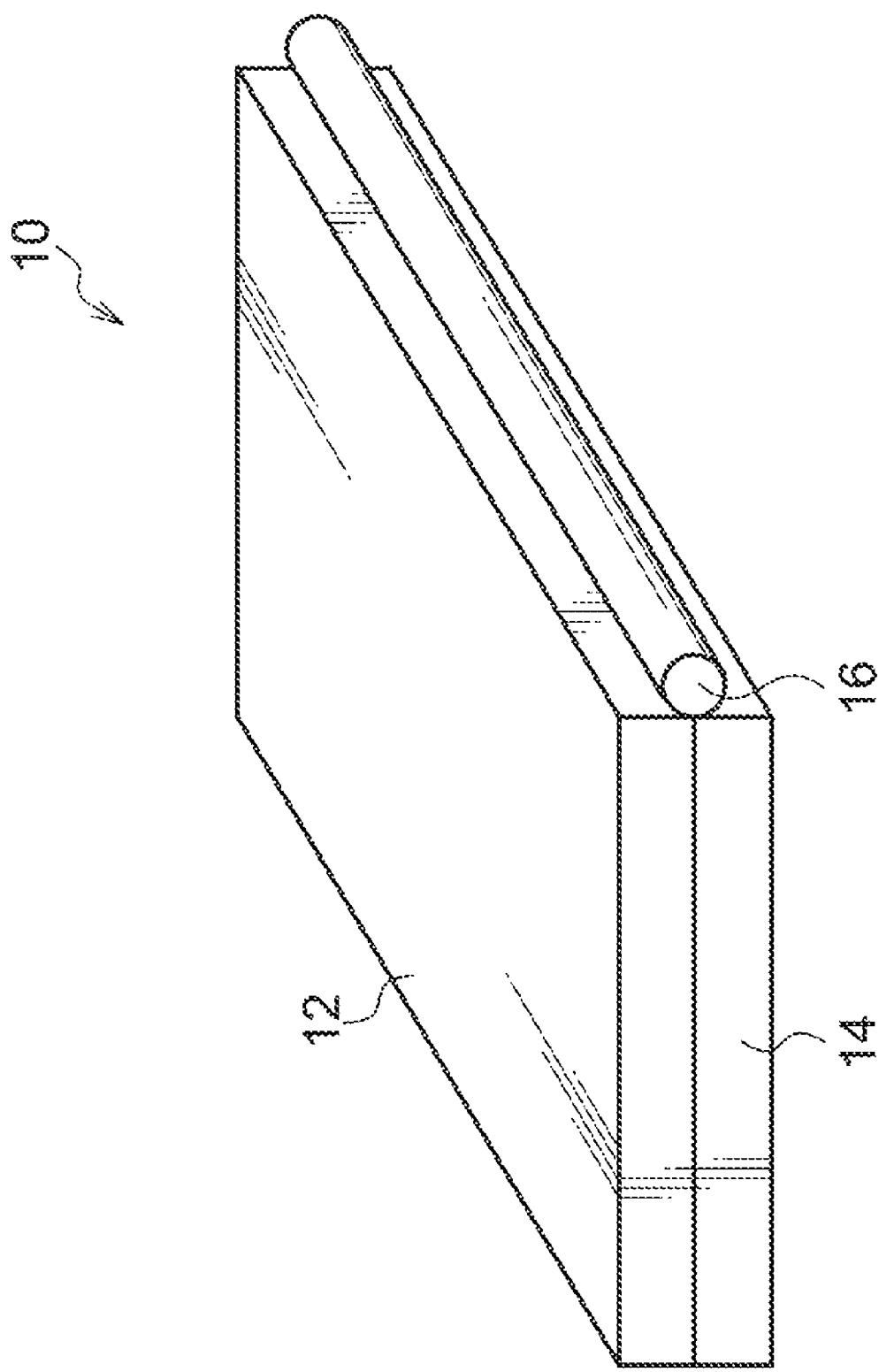
FIG. 1 is a perspective view showing the structure of an electronic cassette in a housed state relating to a first exemplary embodiment.
Figure 2:
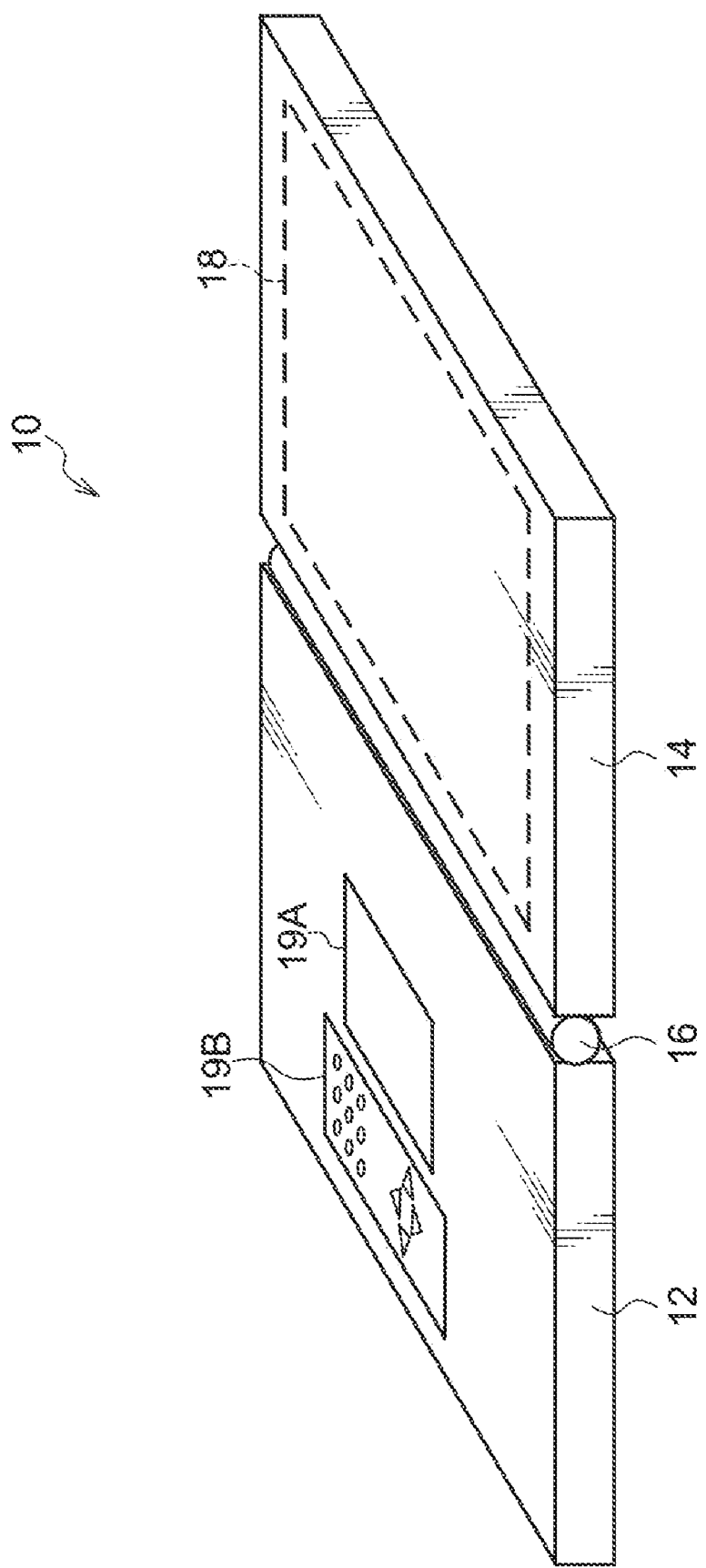
FIG. 2 is a perspective view showing the structure of the electronic cassette in an expanded state relating to the first exemplary embodiment.

Perspective views showing the structure of an electronic cassette 10 relating to a first exemplary embodiment are shown in FIG. 1 and FIG. 2.

As shown in FIG. 1, at the electronic cassette 10, an image capturing unit 12 and a control unit 14 are connected by a hinge 16 so as to be able to open and close. The image capturing unit 12 is shaped as a flat plate, and incorporates a radiation detector 20 (see FIG. 3) therein, and captures radiographic images expressed by irradiated radiation. The control unit 14 incorporates therein a controller 50 that controls the image capturing operations of the radiation detector 20.

Due to one of the image capturing unit 12 and the control unit 14 being rotated around the hinge 16 with respect to the other, the image capturing unit 12 and the control unit 14 can be opened and closed between an expanded state (FIG. 2) in which the image capturing unit 12 and the control unit 14 are lined-up next to one another, and a housed state (FIG. 1) in which the image capturing unit 12 and the control unit 14 are folded-up so as to be superimposed on one another.

Note that, in the first exemplary embodiment, the image capturing unit 12 and the control unit 14 are made to be the same height in order to eliminate a step between the image capturing unit 12 and the control unit 14 in the expanded state (FIG. 2).

The surface of the image capturing unit 12, which surface faces the control unit 14 in the housed state, is a radiation surface 18 onto which radiation is irradiated at the time of capturing a radiographic image.

A display section 19A and an operation panel 19B are provided at the surface of the control unit 14 which surface faces the image capturing unit 12 in the housed state. The display section 19A has a display device that can display images and the like. The operation panel 19B has various types of buttons such as a cross key, a ten key, and the like.

Figure 3:
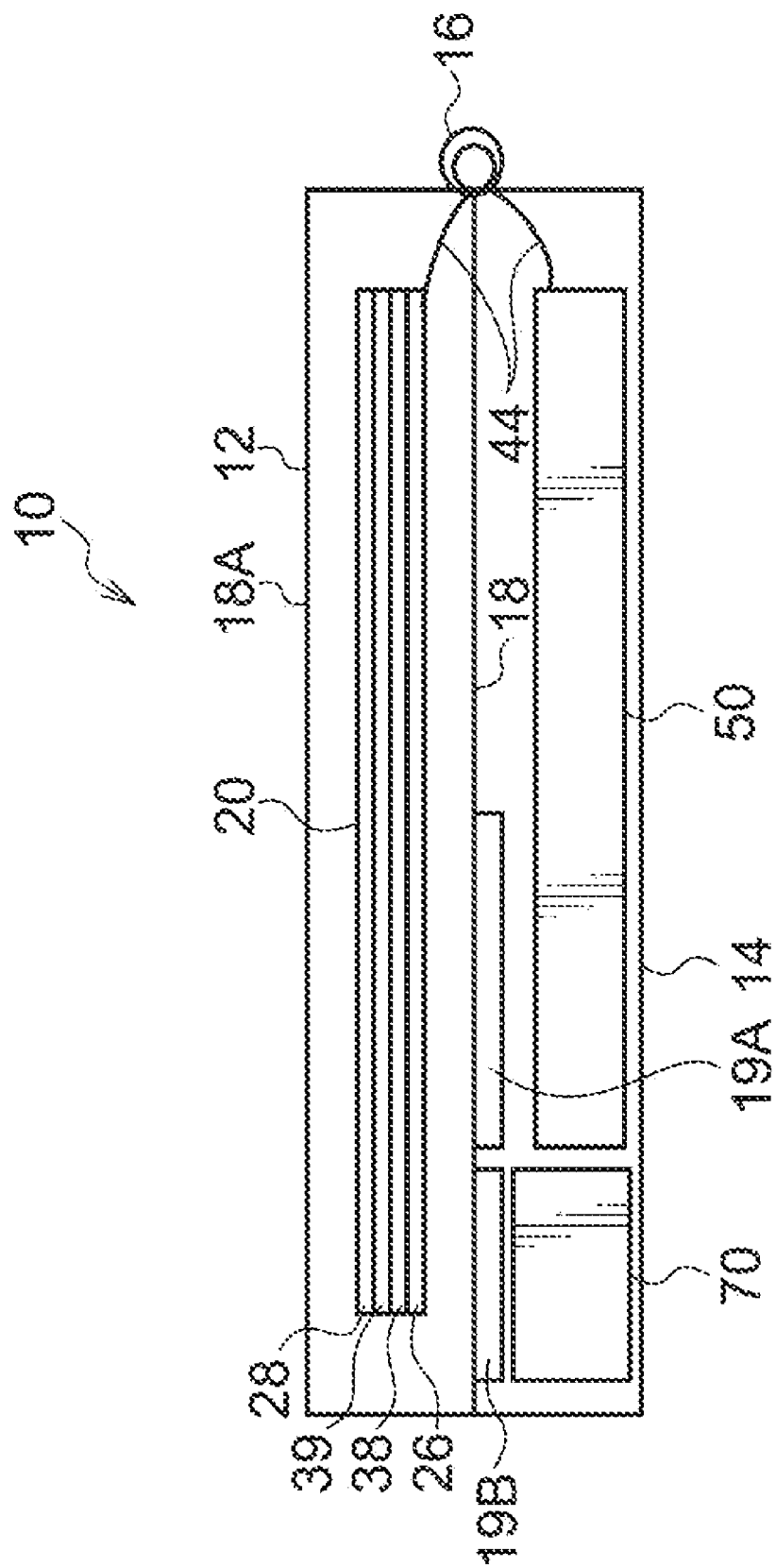
FIG. 3 is a sectional view showing the schematic structure of the electronic cassette in the housed state relating to the first exemplary embodiment.

A sectional view showing the schematic structure of the electronic cassette 10 relating to the first exemplary embodiment is shown in FIG. 3.

The radiation detector 20, that captures a radiographic image expressed by radiation irradiated onto the radiation surface 18 and outputs electric signals expressing the captured radiographic image, is incorporated in the image capturing unit 12.

On the other hand, the controller 50 that controls the image capturing operations of the radiation detector 20, and a power source 70 that supplies electric power to the controller 50, are incorporated in the control unit 14.

The radiation detector 20 and the controller 50 are connected by a connection wire 44 that is provided via the hinge 16.

Figure 4:
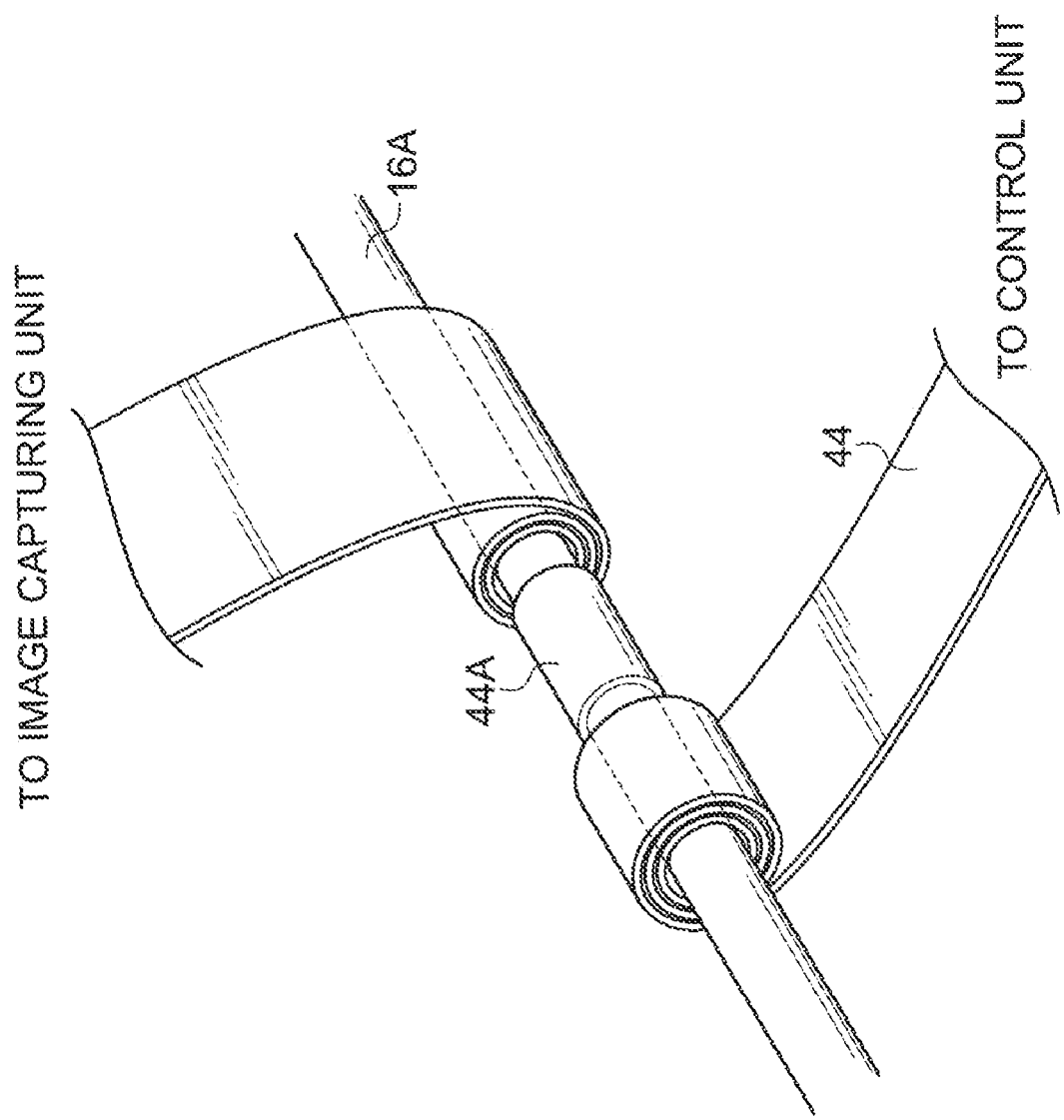
FIG. 4 is a perspective view showing the structure of a connection wire within a hinge relating to the exemplary embodiments.

Because the image capturing unit 12 and the control unit 14 can be opened and closed by the hinge 16, bending or bending stress is constantly applied to the hinge 16 portion of the connection wire 44, and it is easy for disconnection or breakage to arise. Therefore, in the present exemplary embodiment, the connection wire 44 is formed by, for example, a flexible printed substrate or the like. As shown in FIG. 4, the connection wire 44 is wound plural times around a rotation shaft 16A of the hinge 16, that supports the image capturing unit 12 and the control unit 14 such that they can be opened and closed, so as to form a cylindrical tube portion 44A. Tape is wound on the outer periphery thereof so as to hold and fix the cylindrical tube portion 44A. Further, the both sides of the cylindrical tube portion 44A of the connection wire 44 are respectively wound plural times around the rotation shaft 16A spirally and with leeway, and are led-out to the image capturing unit 12 and the control unit 14 respectively.

Due thereto, when the image capturing unit 12 is opened or closed, the connection wire 44 rotates along the rotation shaft 16A. However, because the both sides of the cylindrical tube portion 44A of the connection wire 44 are respectively wound with leeway around the rotation shaft 16A, the connection wire 44 flexibly follows the opening or closing of the image capturing unit 12. Accordingly, the connection wire 44 does not break.

Figure 5:
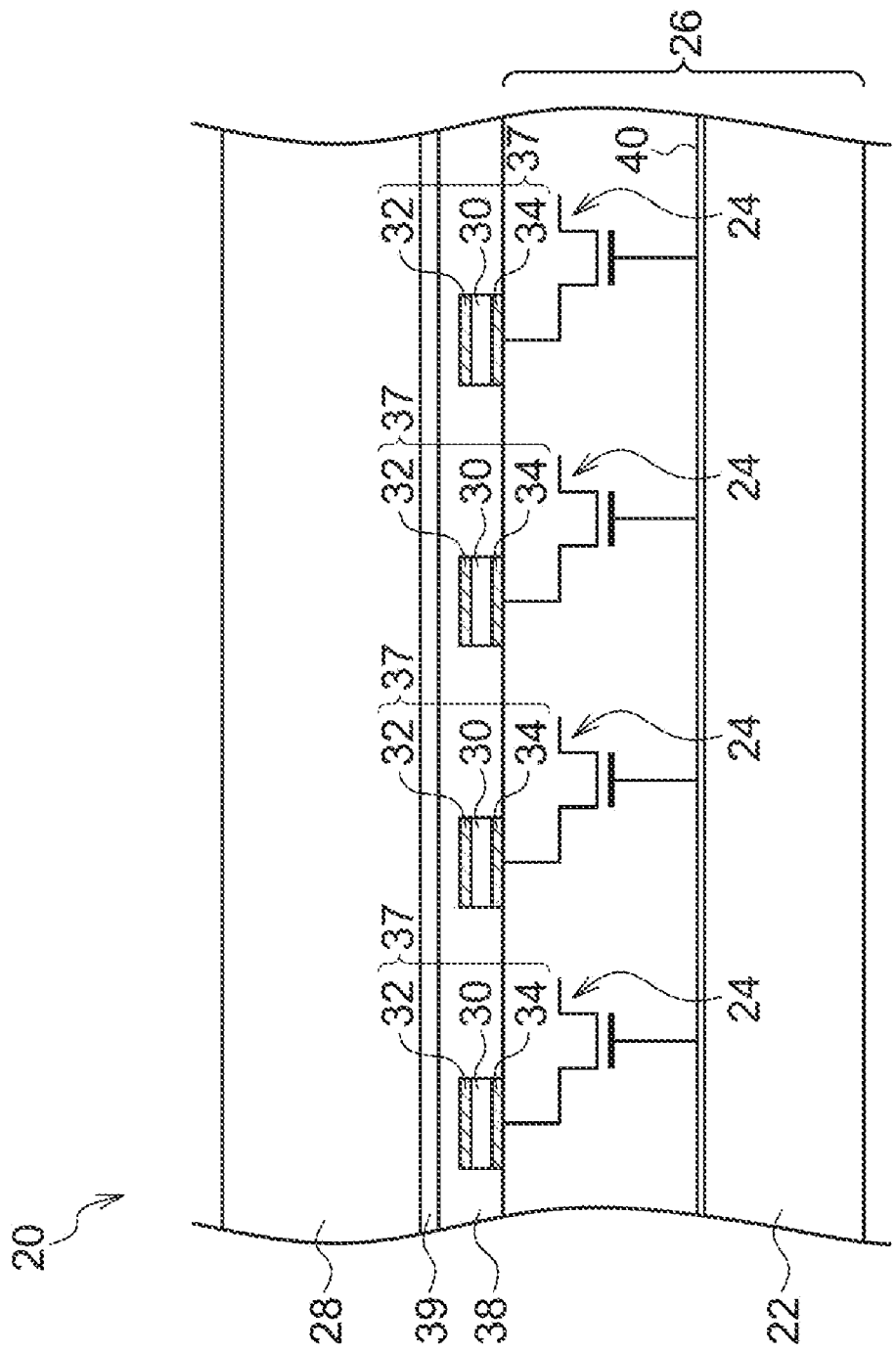
FIG. 5 is a sectional view schematically showing the structure of a radiation detector relating to the exemplary embodiments.
Figure 6:
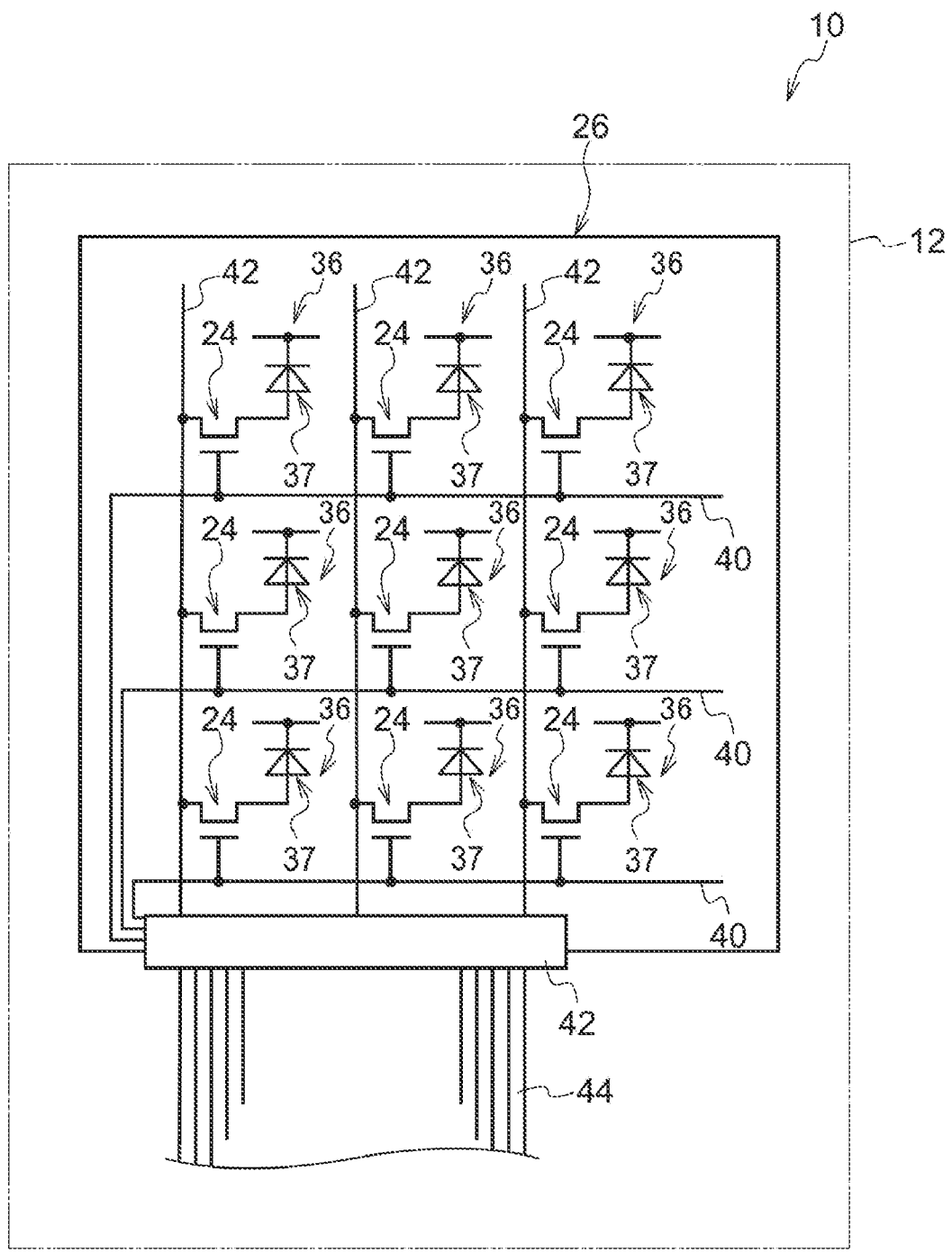
FIG. 6 is a plan view showing the structure of the radiation detector relating to the exemplary embodiments.

The radiation detector 20 relating to the present exemplary embodiment is described next with reference to FIG. 5 and FIG. 6. FIG. 5 is a sectional view schematically showing the structure of the radiation detector 20 relating to the present exemplary embodiment. FIG. 6 is a plan view showing the structure of the radiation detector 20.

As shown in FIG. 5, the radiation detector 20 has a TFT substrate 26 at which switch elements 24 such as thin film transistors (TFTs) or the like are formed on an insulating substrate 22.

A scintillator layer 28, that converts incident radiation into light, is formed on the TFT substrate 26 as an example of a radiation converting layer that converts incident radiation.

For example, CsI:Tl or GOS ($Gd_2O_2S$:Tb) can be used as the scintillator layer 28. Note that the scintillator layer 28 is not limited to these materials.

For example, a glass substrate, any of various types of ceramic substrates, or a resin substrate can be used as the insulating substrate 22. Note that the insulating substrate 22 is not limited to these materials.

Photoconductive layers 30, that generate charges due to the light converted by the scintillator layer 28 being incident thereon, are disposed between the scintillator layer 28 and the TFT substrate 26. Bias electrodes 32 for applying bias voltage to the photoconductive layers 30 are formed on the scintillator layer 28 side surfaces of the photoconductive layers 30.

The photoconductive layer 30 contains an organic photoelectric conversion material, and absorbs light that is emitted from the scintillator layer 28, and generates charges that correspond to the absorbed light. The photoconductive layer 30, that contains an organic photoelectric conversion material in this way, has a sharp absorption spectrum in the visible range, and there is hardly any absorption by the photoconductive layer 30 of electromagnetic waves other than the light emitted by the scintillator layer 28, and noise, that is generated by radiation such as X-rays or the like being absorbed at the photoconductive layer 30, can be effectively suppressed.

In order to efficiently absorb the light that is emitted at the scintillator layer 28, the absorption peak wavelength of the organic photoelectric conversion material that structures the photoconductive layer 30 may be made nearer to the emission peak wavelength of the scintillator layer 28. The absorption peak wavelength of the organic photoelectric conversion material and the emission peak wavelength of the scintillator layer 28 may be made to coincide, but if the difference therebetween is small, the light emitted from the scintillator layer 28 can be absorbed sufficiently. Concretely, the difference between the absorption peak wavelength of the organic photoelectric conversion material and the emission peak wavelength, with respect to radiation, of the scintillator layer 28 may be made within 10 nm, and it is preferable for the difference to be within 5 nm.

Examples of organic photoelectric conversion materials that can satisfy such a condition are, for example, quinacridone organic compounds and phthalocyanine organic compounds. For example, the absorption peak wavelength in the visible range of quinacridone is 560 nm. Therefore, if quinacridone is used as the organic photoelectric conversion material and CsI(Tl) is used as the material of the scintillator layer 28, the aforementioned difference in the peak wavelengths can be made to be within 5 nm, and the amount of charges generated at the photoconductive layer 30 can be made to be substantially the maximum.

Charge collecting electrodes 34, that collect the charges generated at the photoconductive layers 30, are formed at the TFT substrate 26. At the TFT substrate 26, the charges collected at the respective charge collecting electrodes 34 are read-out by the switch elements 24.

As shown in FIG. 6, the charge collecting electrodes 34 are disposed in a two-dimensional form on the TFT substrate 26. The switch elements 24 are disposed in a two-dimensional form at the insulating substrate 22, in correspondence with the charge collecting electrodes 34.

Plural gate lines 40 that extend in a given direction (the row direction) and are for turning the respective switch elements 24 on and off, and plural data lines 42 that extend in a direction (the column direction) orthogonal to the gate lines 40 and are for reading-out the charges via the switch elements 24 that are in on states, are provided at the TFT substrate 26.

A smoothing layer 38 for smoothing the top of the TFT substrate 26 is formed on the TFT substrate 26. Further, an adhesive layer 39 for adhering the scintillator layer 28 to the TFT substrate 26, is formed on the smoothing layer 38 between the TFT substrate 26 and the scintillator layer 28.

The sensor portions 37 that structure the respective pixel portions 36 at the radiation detector 20 can be structured by a bias electrode 32 and a charge collecting electrode 34 that form a pair, and an organic layer that contains the organic photoconductive layer 30 that is sandwiched between the bias electrode 32 and the charge collecting electrode 34. More concretely, this organic layer can be formed by the stacking of or the combining of a region that absorbs electromagnetic waves, a photoelectric conversion region, an electron transport region, a hole transport region, an electron blocking region, a hole blocking region, a crystallization preventing region, electrodes, an interlayer contact improving region, and the like.

The organic layer may contain an organic p-type compound or an organic n-type compound.

An organic p-type semiconductor (compound) is a donor organic semiconductor (compound) exemplified mainly by hole-transporting organic compounds, and means an organic compound that has the property that it easily donates electrons. More specifically, an organic p-type semiconductor (compound) means, when two organic materials are used by being made to contact one another, the organic compound whose ionization potential is smaller. Accordingly, any organic compound can be used as the donor organic compound, provided that it is an electron-donating organic compound.

An organic n-type semiconductor (compound) is an accepter organic semiconductor (compound) exemplified mainly by electron-transporting organic compounds, and means an organic compound that has the property that it easily accepts electrons. More specifically, an organic n-type semiconductor (compound) means, when two organic compounds are used by being made to contact one another, the organic compound whose electron affinity is greater. Accordingly, any organic compound can be used as the accepter organic compound, provided that it is an electron-accepting organic compound.

Materials that can be used as the organic p-type semiconductor and the organic n-type semiconductor, and the structure of the photoconductive layer 30, are described in detail in JP-A No. 2009-32854, and therefore, description thereof is omitted.

Figure 7:
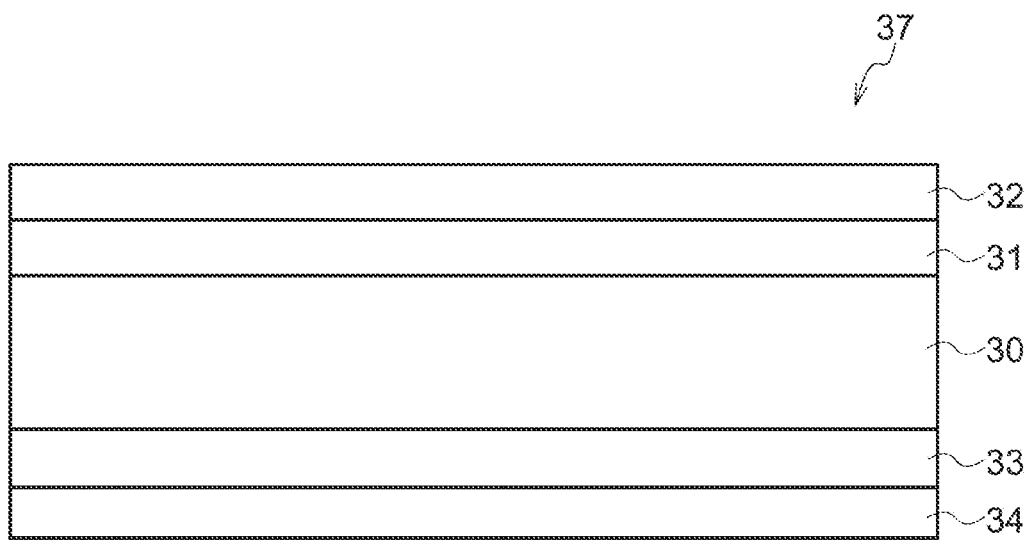
FIG. 7 is a sectional view showing the configuration of the sensor portions relating to the exemplary embodiments.

Here, it suffices for the sensor portion 37 that structures each pixel portion 36 to include at least the charge collecting electrode 34, the photoconductive layer 30 and the bias electrode 32. However, in order to suppress an increase in dark current, as shown in FIG. 7, it is preferable that the sensor portion 37 be provided with at least one of an electron blocking film 33 and a hole blocking film 31, and it is more preferable that the sensor portion 37 be provided with the both.

The electron blocking film 33 can be provided between the charge collecting electrode 34 and the photoconductive layer 30. The electron blocking film 33 can suppress the injection of electrons from the charge collecting electrode 34 into the photoconductive layer 30 and an increase in dark current, when bias voltage is applied between the charge collecting electrode 34 and the bias electrode 32.

An electron-donating organic material can be used for the electron blocking film 33. It suffices to select the material, that is actually used for the electron blocking film 33, in accordance with the material of the electrode adjacent thereto, the material of the photoconductive layer 30 adjacent thereto, and the like. It is preferable that the material have an electron affinity (Ea) that is 1.3 eV or more greater than the work function (Wf) of the material of the electrode adjacent thereto, and have an ionization potential (Ip) that is equal to or smaller than the ionization potential of the material of the photoconductive layer 30 adjacent thereto. Materials that can be used as this electron-donating organic material are described in detail in JP-A No. 2009-32854, and therefore, description thereof is omitted. In order to reliably exhibit a dark current suppressing effect and to prevent a decrease in the photoelectric conversion efficiency of the sensor portion 37, it is preferable that the thickness of the electron blocking film 33 be from 10 nm to 200 nm, and more preferable that the thickness be from 30 nm to 150 nm, and particularly preferable that the thickness be from 50 nm to 100 nm.

The hole blocking film 31 can be provided between the photoconductive layer 30 and the bias electrode 32. The hole blocking film 31 can suppress the injecting of holes from the bias electrode 32 into the photoconductive layer 30 and an increase in dark current, when bias voltage is applied between the charge collecting electrode 34 and the bias electrode 32.

An electron-accepting organic material can be used for the hole blocking film 31. In order to reliably exhibit a dark current suppressing effect and to prevent a decrease in the photoelectric conversion efficiency of the sensor portion 37, it is preferable that the thickness of hole blocking film 31 be from 10 nm to 200 nm, and more preferable that the thickness be from 30 nm to 150 nm, and particularly preferable that the thickness be from 50 nm to 100 nm.

Figure 8:
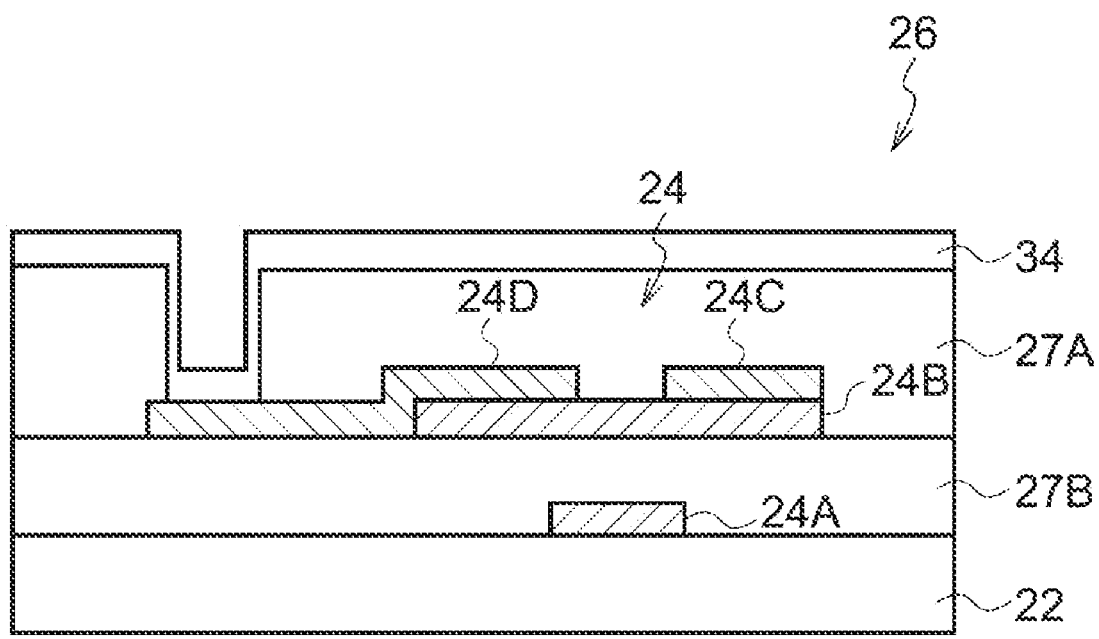
FIG. 8 is a sectional view showing the configuration of switch elements formed on the TFT substrates relating to the exemplary embodiments.

It suffices to select the material, that is actually used for the hole blocking film 31, in accordance with the material of the electrode adjacent thereto, the material of the photoconductive layer 30 adjacent thereto, and the like. It is preferable that the material have an ionization potential (Ip) that is 1.3 eV or more greater than the work function (Wf) of the material of the electrode adjacent thereto, and have an electron affinity (Ea) that is equal to or greater than the electron affinity of the material of the photoconductive layer 30 adjacent thereto. Materials that can be used as this electron-accepting organic material are described in detail in JP-A No. 2009-32854, and therefore, description thereof is omitted. The structure of the switch element 24 that is formed at the TFT substrate 26 relating to the present exemplary embodiment is shown schematically in FIG. 8.

The switch element 24 is formed on the insulating substrate 22 so as to correspond to the charge collecting electrode 34. The region at which the switch element 24 is formed has, in plan view, a portion that is superposed with the charge collecting electrode 34. Due to such a structure, the storage capacitor 68, the switching element 24 and the sensor portion 72 at each pixel portion are superposed in the thickness direction, and the storage capacitor 68, the switch element 24 and the sensor portion 72 can be disposed in a small surface area. The switching element 24 is electrically connected to the corresponding charge collecting electrode 34, via wiring of an electrically-conductive material that is formed so as to pass-through an insulating film 27A that is provided between the insulating substrate 22 and the charge collecting electrode 34. Due thereto, the charges collected at the charge collecting electrode 34 can be moved to the switch element 24.

At the switch element 24, a gate electrode 24A, a gate insulating film 27B and an active layer (channel layer) 24B are layered, and further, the switch element 24 is structured as a thin-film transistor at which a source electrode 24C and a drain electrode 24D are formed on the active layer 24B with a predetermined interval therebetween. At the radiation detector 20, the active layer 24B is formed of an amorphous oxide. As the amorphous oxide that structures the active layer 24B, oxides containing at least one of In, Ga and Zn (e.g., In—O types) are preferable, oxides containing at least two of In, Ga and Zn (e.g., In—Zn—O types, In—Ga—O types, Ga—Zn—O types) are more preferable, and oxides containing In, Ga and Zn are particularly preferable. As an In—Ga—Zn—O type amorphous oxide, amorphous oxides whose composition in a crystal state is expressed by $InGaO_3(ZnO)_m$ (where m is a natural number of less than 6) are preferable, and in particular, $InGaZnO_4$ is more preferable.

If the active layer 24B of the switch element 24 is formed by an amorphous oxide, radiation such as X-rays and the like is not absorbed, or even if absorbed, only an extremely small amount will be absorbed. Therefore, the occurrence of noise at the signal outputting section 14 can be effectively suppressed.

Here, both the amorphous oxide that structures the active layer 24B of the switch element 24 and the organic photoelectric conversion material that structures the above-described photoconductive layer 30 can be formed as films at low temperatures. Accordingly, the insulating substrate 22 is not limited to a highly heat-resistant substrate such as a semiconductor substrate, a quartz substrate, a glass substrate or the like, and a flexible substrate of plastic or the like, and aramid and bio-nanofibers can be used. Concretely, flexible substrates of polyesters such as polyethylene terephthalate, polybutylene phthalate, polyethylene naphthalate and the like, polystyrene, polycarbonate, polyethersulfone, polyarylate, polyimide, polycycloolefin, norbornene resin, poly(chlorotrifluoroethylene), and the like can be used. If a flexible substrate made of such a plastic is used, the radiation detector 20 can be made to be lightweight, which is favorable for, for example, carrying the electronic cassette 10, and the like.

Further, an insulating layer for ensuring the insulating ability, a gas barrier layer for preventing the transmission of moisture and oxygen, an undercoat layer for improving the flatness and the adhesiveness with the electrodes and the like, and the like may be provided at the insulating substrate 22.

High-temperature processes of 200° or more can be applied to aramid. Therefore, the transparent electrode material can be hardened at a high temperature and made to have low resistance, and further, automatic packaging of a driver IC, including a solder reflow step, also can be handled. Moreover, because the coefficient of thermal expansion of aramid is near to those of ITO (indium tin oxide) and glass substrates, there is little warping after manufacture, and the substrate is difficult to break. In addition, as compared with a glass substrate and the like, a thin substrate can be formed by using aramid. Note that the insulating substrate 22 may be formed by layering an ultra-thin glass substrate and aramid. Bio-nanofibers are fibers in which a cellulose microfibril bundle (bacteria cellulose) that can produce bacteria (acetic acid bacterium, *Acetobacter Xylinum*), and a transparent resin are compounded. The cellulose microfibril bundle has a width of 50 nm which is a size of 1/10 with respect to the visible light wavelength, and has high strength, high elasticity, and low thermal expansion. By impregnating and hardening a transparent resin, such as acrylic resin, epoxy resin or the like, in bacteria cellulose, bio-nanofibers that contain up to 60 to 70% fiber while still exhibiting light transmittance of about 90% at a wavelength of 500 nm, are obtained. Bio-nanofibers have a low coefficient of thermal expansion (3-7 ppm) that is comparable to that of silicon crystal, have strength (460 MPa) to the same extent as that of steel, have high elasticity (30 GPa), and are flexible. Therefore, the insulating substrate 22 can be formed to be thin as compared with a glass substrate or the like.

The TFT substrate 26 is, in plan view as shown in FIG. 6, formed in the shape of a quadrilateral having four sides at the outer edge. Specifically, the TFT substrate 26 is rectangular.

A connection terminal 42, to which the individual gate lines 40 and the individual data lines 42 are connected, is disposed at one side at the peripheral end portion of the TFT substrate 26 as seen in plan view.

The connection terminal 42 is connected to the controller 50 via the connection wire 44.

Here, at the radiation detector 20, when the radiation X is irradiated from the obverse side at which the scintillator layer 28 is formed (obverse irradiation), light is emitted more strongly at the top surface side (the side opposite the TFT substrate 26) of the scintillator layer 28. When the radiation X is irradiated from the TFT substrate 26 side (the reverse side) (reverse irradiation), the radiation X that is transmitted through the TFT substrate 26 is incident on the scintillator layer 28, and the TFT substrate 26 side of the scintillator layer 28 emits light more strongly. Charges are generated at the respective sensor portions 37 provided at the TFT substrate 26, due to the light that is generated at the scintillator layer 28. Therefore, at the radiation detector 20, the light-emitting position of the scintillator layer 28 with respect to the TFT substrate 26 is closer in the case in which the radiation X is irradiated from the reverse side than in the case in which the radiation X is irradiated from the obverse side. Therefore, the resolution of the radiographic image obtained by image capturing is high.

In the electronic cassette 10 relating to the present exemplary embodiment, as shown in FIG. 3, the radiation detector 20 is disposed within the image capturing unit 12 such that the TFT substrate 26 is at the irradiated surface 18 side. Accordingly, the radiation that is irradiated from the irradiated surface 18 side is irradiated onto the reverse of the radiation detector 20.

Figure 9:
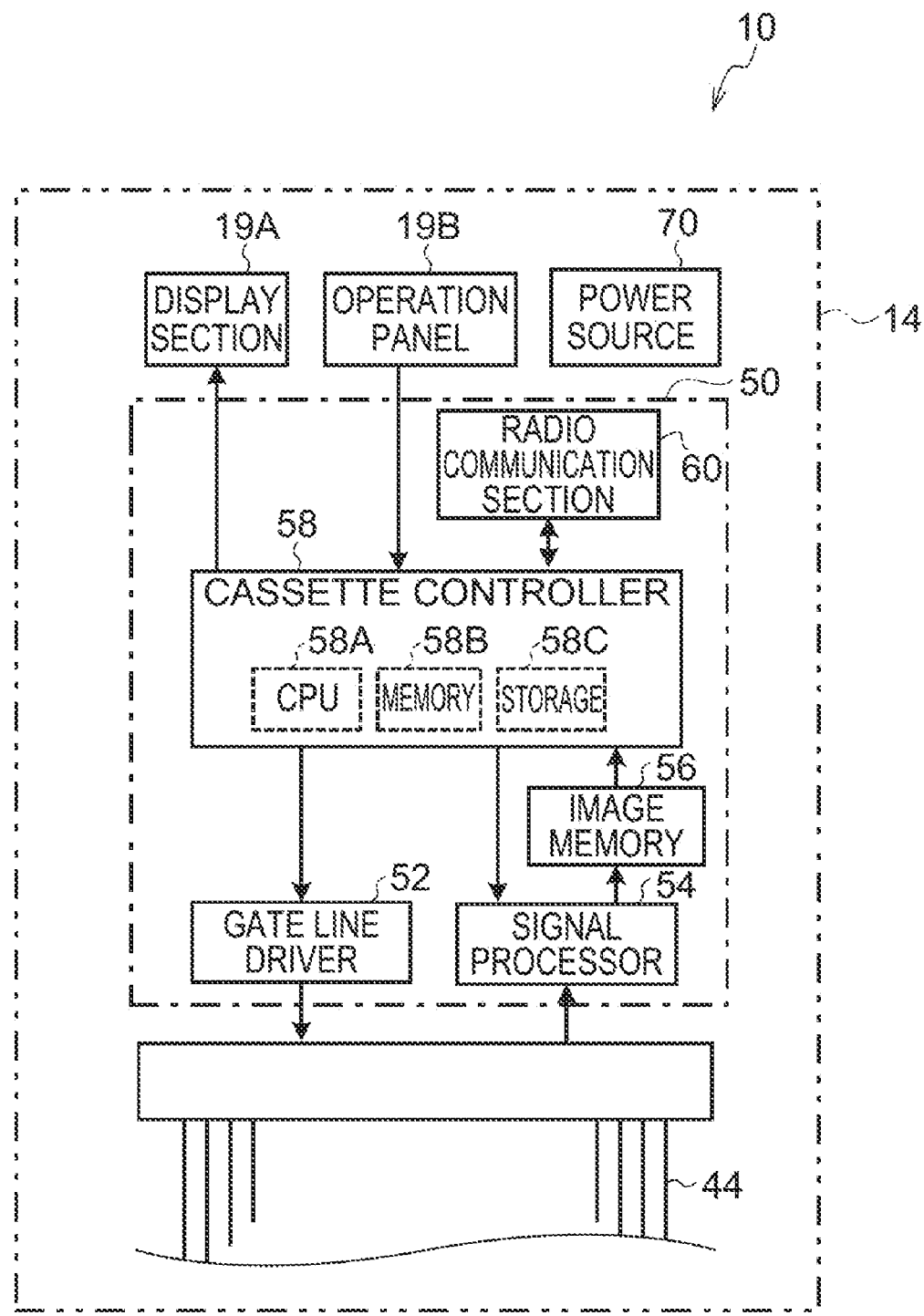
FIG. 9 is a block diagram showing the schematic structure of a controller relating to the exemplary embodiments.

A block diagram showing the schematic structure of the controller 50 relating to the present exemplary embodiment is shown in FIG. 9.

As shown in FIG. 9, the controller 50 has a gate line driver 52, a signal processor 54, an image memory 56, a cassette controller 58, and a radio communication section 60.

The respective switch elements 24 (FIG. 5 and FIG. 6) are turned on in order in units of rows by signals that are supplied from the gate line driver 52 via the gate lines 40. The charges read-out by the switch elements 24 that have been turned on are transferred to the data lines 42 as electric signals, and are inputted to the signal processor 54. Due thereto, the charges are read-out in order in units of rows, and a two-dimensional radiographic image can be acquired.

Although not illustrated, the signal processor 54 has, for each of the individual data lines 42, an amplifying circuit, that amplifies the inputted electric signal, and a sample/hold circuit. After the electric signals transferred through the individual data lines 42 are amplified at the amplifying circuits, the signals are held in the sample/hold circuits. Further, a multiplexer and an A/D (analog/digital) converter are connected in that order to the output sides of the sample/hold circuits. The electric signals held in the individual sample/hold circuits are inputted in order (serially) to the multiplexer, and are converted into digital image data by the A/D converter.

The image memory 56 is connected to the signal processor 54. The image data, that is outputted from the A/D converter of the signal processor 54, is stored in order in the image memory 56. The image memory 56 has a storage capacity that can store image data of a predetermined number of images. Each time that capturing of a radiographic image is carried out, the image data obtained by the image capturing is successively stored in the image memory 56.

The image memory 56 is connected to the cassette controller 58. The cassette controller 58 is structured by a microcomputer, and has a CPU (Central Processing Unit) 58A, a memory 58B including a ROM and a RAM, and a non-volatile storage 58C formed by a flash memory or the like. The cassette controller 58 controls the operations of the entire electronic cassette 10.

The radio communication section 60 is connected to the cassette controller 58. The radio communication section 60 corresponds to wireless LAN (Local Area Network) standards exemplified by IEEE (Institute of Electrical and Electronics Engineers) 802.11a/b/g or the like. The radio communication section 60 controls the transfer of various types of information to and from external devices by radio communication. The cassette controller 58 can, via the radio communication section 60, communicate by radio with an external device that controls the overall radiographic image capturing such as a console or the like. Accordingly, the cassette controller 58 can carry out transmission and reception of various types of information to and from the console. The cassette controller 58 stores various types of information, such as image capturing conditions, patient information, and the like that are received from the console via the radio communication section 60, and starts reading-out of the charges on the basis of the image capturing conditions.

The display section 19A and the operation panel 19B are respectively connected to the cassette controller 58. The cassette controller 58 controls the display of various types of information on the display section 19A, and can know of the contents of operation with respect to the operation panel 19B.

As mentioned above, the power source 70 is provided at the electronic cassette 10. The above-described various types of circuits and respective elements (the display section 19A, the operation panel 19B, the gate line driver 52, the signal processor 54, the image memory 56, the radio communication section 60, and the microcomputer that functions as the cassette controller 58), are operated by electric power supplied from the power source 70. So that the portability of the electronic cassette 10 is not adversely affected, the power source 70 incorporates therein a battery (a chargeable secondary battery) and supplies electric power from the charged battery to the various types of circuits and elements. Note that illustration of the wires that connect the power source 70 with the various types of circuits and respective elements is omitted from FIG. 9.

Operation of the electronic cassette 10 relating to the first exemplary embodiment is described next.

As shown in FIG. 1 and FIG. 3, the electronic cassette 10 is transported in the housed state in which the image capturing unit 12 and the control unit 14 are folded-up and stacked one on another. At the electronic cassette 10 relating to the present exemplary embodiment, in the housed state, the radiation surface 18 is at the inner side and is protected in this way. Therefore, damage to the radiation surface 18 when the electronic cassette 10 is carried around can be prevented.

On the other hand, when a radiographic image is to be captured, the electronic cassette 10 is set in the expanded state in which the image capturing unit 12 and the control unit 14 are lined-up next to one another as shown in FIG. 2. Further, the electronic cassette 10 receives image capturing conditions and patient information from the console via the radio communication section 60. When the patient information is received, the cassette controller 58 displays, on the display section 19A, information (e.g., the name or ID of the patient) relating to the patient that is based on the received patient information. In this way, at the electronic cassette 10 relating to the present exemplary embodiment, because the name or ID is displayed on the display section 19A, the radiologic technician can reliably confirm whether or not there is mistaken identification of the patient on whom radiographic image capturing is to be carried out, by, for example, the radiologic technician confirming the name with the patient himself/herself, and comparing the confirmed name with the name displayed on the screen, or the like.

Figure 10:
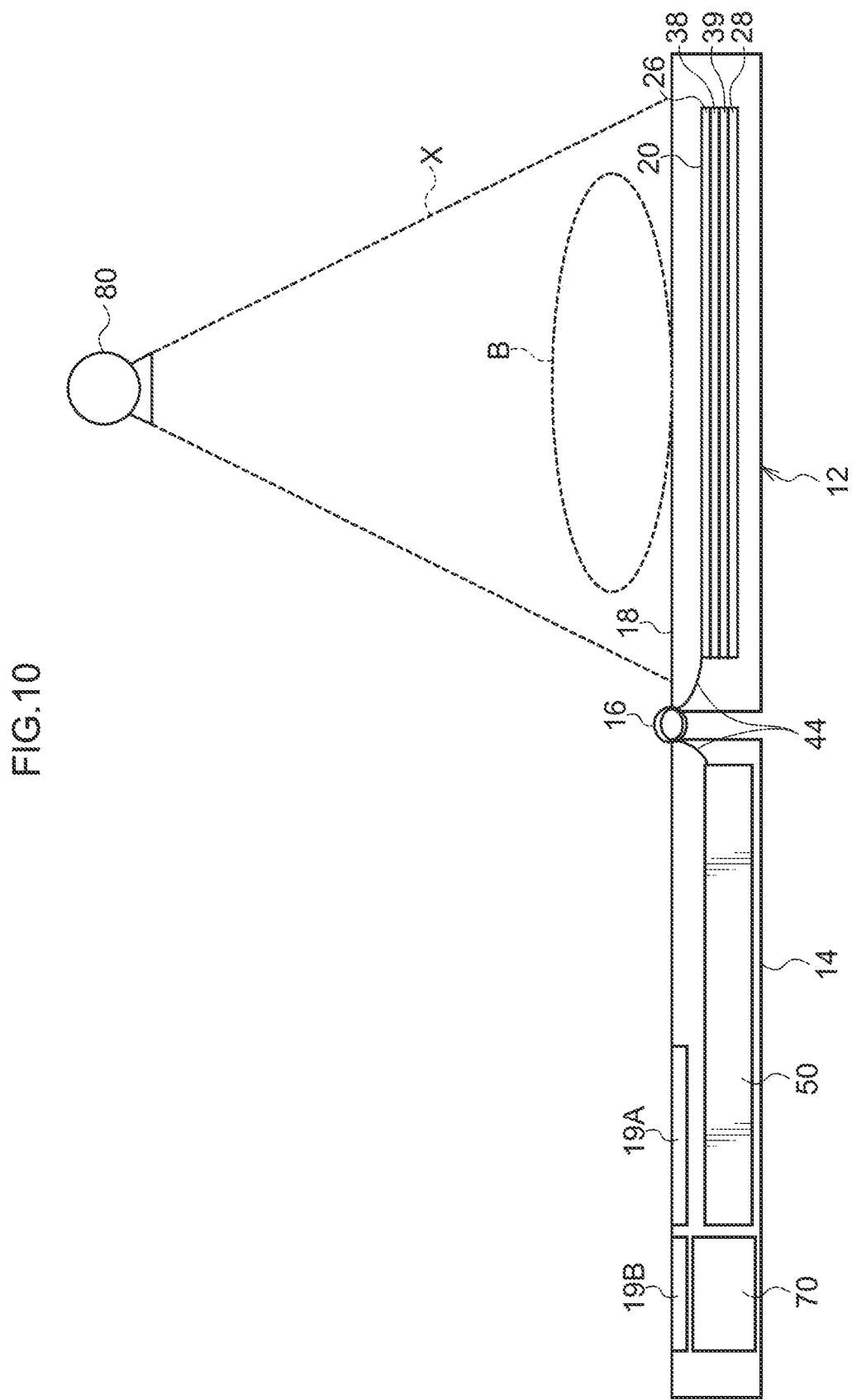
FIG. 10 is a sectional view showing the state of placement when carrying out image capturing at the electronic cassette relating to the first exemplary embodiment.

When the radiologic technician finishes confirming the patient, as shown in FIG. 10, the electronic cassette 10 is disposed such that there is an interval between the electronic cassette 10 and a radiation generating device 80 that generates radiation, and a region B that is the object of image capturing of the patient is placed on the radiation surface 18. The radiation generating device 80 irradiates radiation of a radiation amount corresponding to image capturing conditions and the like that were provided in advance. Due to the radiation X emitted from the radiation generating device 80 passing through the region B that is the object of image capturing, the radiation X carries image information, and thereafter, is irradiated onto the electronic cassette 10.

The radiation X that is irradiated from the radiation generating device 80 passes through the region B that is the object of image capturing, and thereafter, reaches the electronic cassette 10. Due thereto, charges, that correspond to the radiation amount of the irradiated radiation X, are collected and accumulated in the respective charge collecting electrodes 34 of the radiation detector 20 that is incorporated within the electronic cassette 10.

After irradiation of the radiation X is finished, the cassette controller 58 controls the gate line driver 52 such that ON signals are outputted from the gate line driver 52 to the respective gate lines 40 in order and line-by-line, and the respective switch elements 24 that are connected to the respective gate lines 40 are turned on in order and line-by-line. Due thereto, the charges that are accumulated in the respective charge collecting electrodes 34 flow-out in order and line-by-line to the respective data lines 42 as electric signals. The electric signals, that have flowed-out to the respective data lines 42, are inputted to the signal processor 54, are converted into digital image information, and are stored in the image memory 56.

At the electronic cassette 10 relating to the present exemplary embodiment, the radiation, that is transmitted through the irradiated surface 18, is irradiated onto the reverse of the radiation detector 20. Therefore, a radiographic image of a high resolution can be captured.

Further, at the radiation detector 20, the photoconductive layer 30 is structured of an organic photoelectric conversion material, and hardly any radiation is absorbed at the photoconductive layer 30. Therefore, the radiation detector 20 is suited to reverse irradiation.

Moreover, the amorphous oxide that structures the active layer 24B of the switch element 24 and the organic photoelectric conversion material that structures the photoconductive layer 30 can both be formed as films at low temperature. Therefore, the insulating substrate 22 can be formed of a plastic resin, aramid, or bio-nanofibers at which there is little absorption of radiation. Because the absorbed amount of radiation at the insulating substrate 22 that is formed in this way is small, a decrease in sensitivity with respect to the radiation X can be suppressed even when radiation is transmitted through the TFT substrate 26 by reverse irradiation.

After image capturing is finished, the cassette controller 58 transmits the image information stored in the image memory 56 to the console. Note that, although the present exemplary embodiment describes a case of capturing a still image, video image capturing may be carried out by carrying out image capturing continuously.

In this way, by setting the electronic cassette 10 relating to the present exemplary embodiment in the expanded state when carrying out image capturing, transmission of the heat, that is generated at the controller 50 within the control unit 14, to the radiation detector 20 within the image capturing unit 12 can be suppressed. Therefore, changes in the characteristics of the radiation detector 20 are suppressed, the image quality of the radiographic image that is captured is stable, and, further, the durability of the radiation detector 20 improves. Because the image capturing unit 12 contacts the patient at the time of capturing a radiographic image, by suppressing the transmission of heat that is generated at the controller 50 to the image capturing unit 12, it is possible to prevent the surface temperature of the image capturing unit 12 from becoming too high and the patient from feeling uncomfortable. Moreover, because the radiation detector 20 is a layered structure and the coefficients of thermal expansion of the members structuring the respective layers are different, the occurrence of deformation or breakage due to heat, and the adhesive deteriorating and peeling due to temperature cycles, can be suppressed.

Further, at the time of carrying out image capturing, it suffices to set the electronic cassette 10 relating to the present exemplary embodiment in the expanded state, and to place only the image capturing unit 12 at the region B that is the object of image capturing. Accordingly, because the thickness of the electronic cassette 10 becomes thinner due to the expanding, it is easy to insert the electronic cassette 10, for example, even beneath a patient who is lying down.

At the electronic cassette 10 relating to the present exemplary embodiment, the control unit 14 is apart spatially from the region B that is the object of image capturing. Therefore, even if a cooling fan for forcible cooling is provided at the control unit 14, the air does not directly hit the patient.

Further, by setting the electronic cassette 10 relating to the present exemplary embodiment in the expanded state when carrying out image capturing, the surface area increases, and therefore, the heat dissipating effect improves. When capturing video images in particular, the amount of heat that is generated is large, and therefore, the surface area being larger is preferable from the standpoint of heat dissipation. The heat dissipating effect may be further improved by forming the surface of the control unit 14 to have convex and concave shapes so as to increase the surface area. The convex and concave shapes may be any of wave shapes, hemispherical shapes, or the like.

At the electronic cassette 10 relating to the present exemplary embodiment, the control unit 14 can be removed from the region onto which the radiation X is irradiated. Therefore, heavy metals for preventing exposure to radiation are not needed, and the electronic cassette 10 can be made to be light-weight and thin.

Moreover, at the electronic cassette 10 relating to the present exemplary embodiment, the radio communication section 60 is provided within the control unit 14 that is away from the patient when the electronic cassette 10 is set in the expanded state. Because the antenna is away from the patient when radio communication is carried out, it is difficult for radio interference to occur.

Second Exemplary Embodiment

A second exemplary embodiment is described next.

Figure 11:
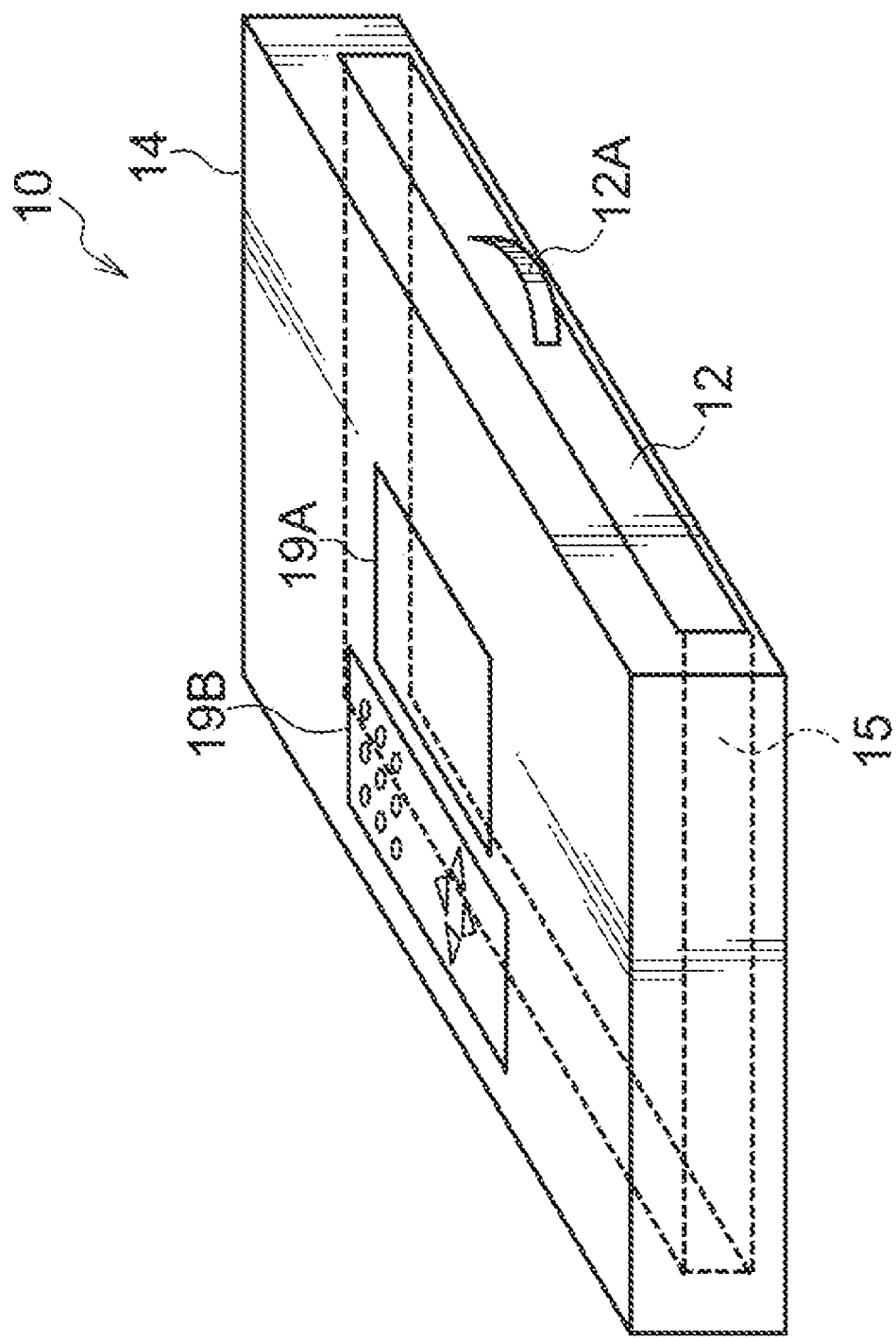
FIG. 11 is a perspective view showing the structure of an electronic cassette in a housed state relating to a second exemplary embodiment.
Figure 12:
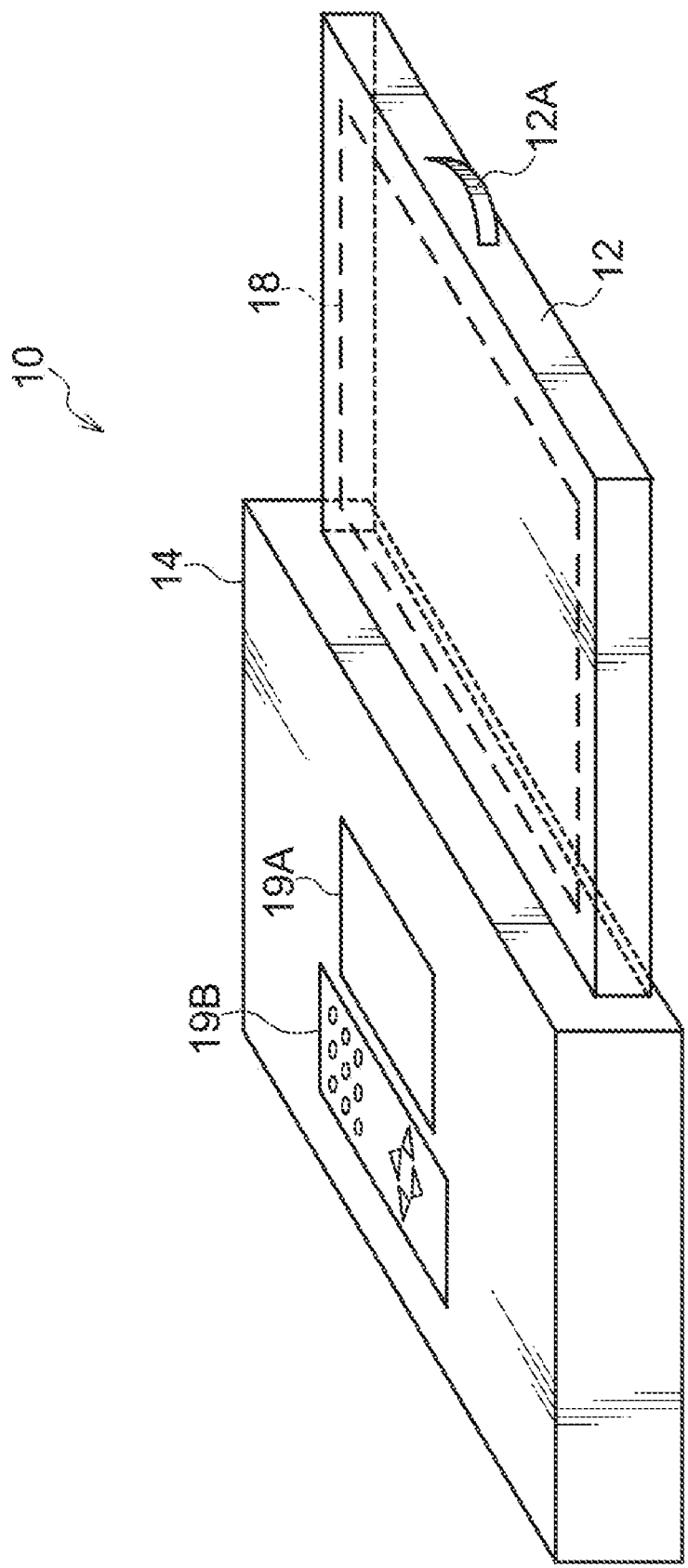
FIG. 12 is a perspective view showing the structure of the electronic cassette in an expanded state relating to the second exemplary embodiment.

Perspective views showing the structure of the electronic cassette 10 relating to the second exemplary embodiment are shown in FIG. 11 and FIG. 12. Note that portions corresponding to those of the above-described first exemplary embodiment (see FIG. 1) are denoted by the same reference numerals. Further, because the structure of the radiation detector 20 and the schematic structure of the controller 50 are the same as in the first exemplary embodiment, description thereof is omitted.

As shown in FIG. 11, an accommodating portion 15 that can accommodate the image capturing unit 12 therein is provided in the control unit 14 of the electronic cassette 10. The electronic cassette 10 can be changed between a housed state (FIG. 11) in which the image capturing unit 12 is housed in the accommodating portion 15, and an expanded state (FIG. 12) in which the image capturing unit 12 is pulled-out from the accommodating portion 15.

The top surface of the image capturing unit 12 is the radiation surface 18 onto which radiation is irradiated at the time of capturing a radiographic image. Further, a handle portion 12A, that is grasped when the image capturing unit 12 is to be pulled-out from the accommodating portion 15, is provided at a side surface of the image capturing unit 12 which side surface is exposed to the exterior in the housed state in which the image capturing unit 12 is accommodated in the accommodating portion 15.

The display section 19A and the operation panel 19B are provided at the top surface of the control unit 14.

Figure 13:
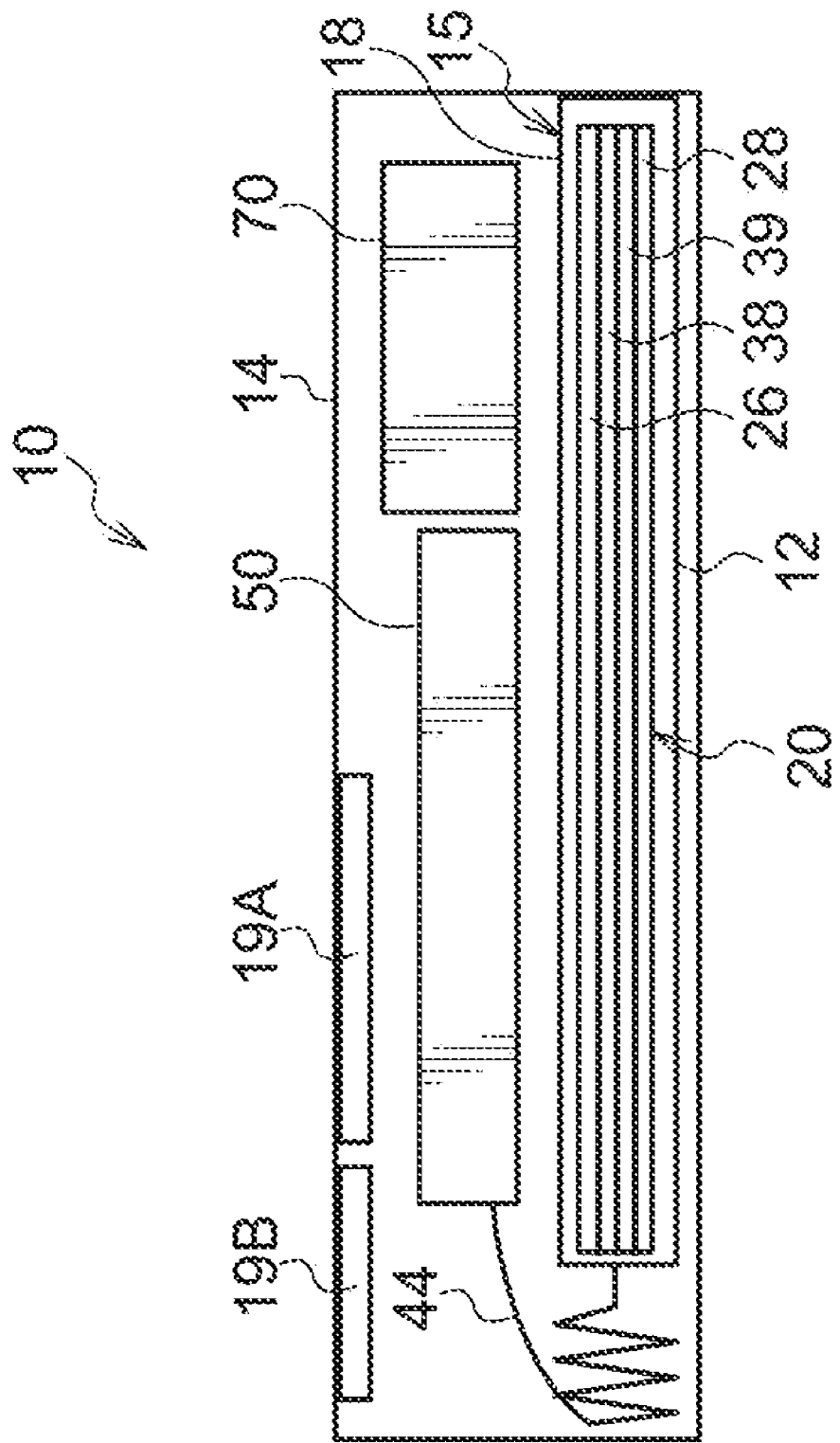
FIG. 13 is a sectional view showing the schematic structure of the electronic cassette in the housed state relating to the second exemplary embodiment.

A sectional view showing the schematic structure of the electronic cassette 10 relating to the second exemplary embodiment is shown in FIG. 13.

The radiation detector 20, that captures a radiographic image expressed by radiation irradiated onto the radiation surface 18 and outputs electric signals expressing the captured radiographic image, is incorporated in the image capturing unit 12 at the inner side of the radiation surface 18.

Also in the electronic cassette 10 relating to the present exemplary embodiment, the radiation detector 20 is disposed within the image capturing unit 12 such that the TFT substrate 26 is at the irradiated surface 18 side. Accordingly, the radiation, that is irradiated from the irradiated surface 18 side, is irradiated onto the reverse of the radiation detector 20.

On the other hand, the controller 50 that controls the image capturing operations of the radiation detector, and the power source 70, are incorporated in the control unit 14.

The radiation detector 20 and the controller 50 are connected via the flexible connection wire 44 that is formed by a printed wiring board or the like.

Operation of the electronic cassette 10 relating to the second exemplary embodiment is described next.

As shown in FIG. 11 and FIG. 13, the electronic cassette 10 is transported in the housed state in which the image capturing unit 12 is accommodated in the accommodating portion 15. In this way, at the electronic cassette 10 relating to the present exemplary embodiment, in the housed state, the radiation surface 18 is at the inner side and is protected. Therefore, damage to the radiation surface 18 when the electronic cassette 10 is carried around can be prevented.

Figure 14:
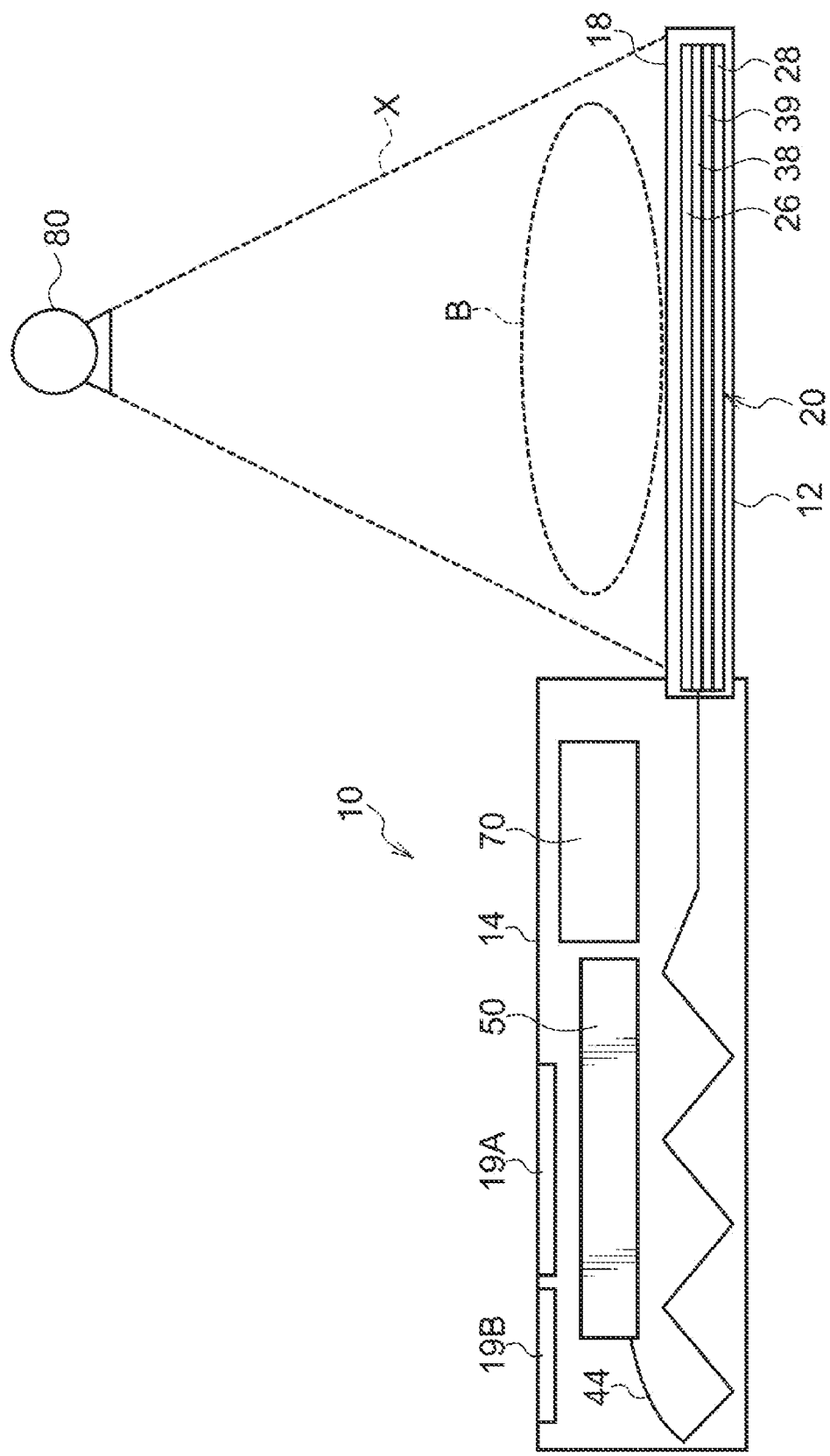
FIG. 14 is a sectional view showing the state of placement when carrying out image capturing at the electronic cassette relating to the second exemplary embodiment.

On the other hand, when a radiographic image is to be captured, as shown in FIG. 12, the electronic cassette 10 is set in the expanded state in which the image capturing unit 12 is pulled-out from the accommodating portion 15. As shown in FIG. 14, the electronic cassette 10 is disposed such that there is an interval between the electronic cassette 10 and a radiation generating device 80, and the region B that is the object of image capturing of the patient is placed on the radiation surface 18.

By setting the electronic cassette 10 relating to the present exemplary embodiment in the expanded state in this way when carrying out image capturing, transmission of the heat, that is generated at the controller 50 within the control unit 14, to the radiation detector 20 within the image capturing unit 12 can be suppressed. Therefore, changes in the characteristics of the radiation detector 20 are suppressed, the image quality of the radiographic image that is captured is stable, and, further, the durability of the radiation detector 20 improves.

Further, in the electronic cassette 10 relating to the present exemplary embodiment, because the radiation that is transmitted through the irradiated surface 18 is irradiated onto the reverse of the radiation detector 20, a radiographic image of a high resolution can be captured.

Figure 15:
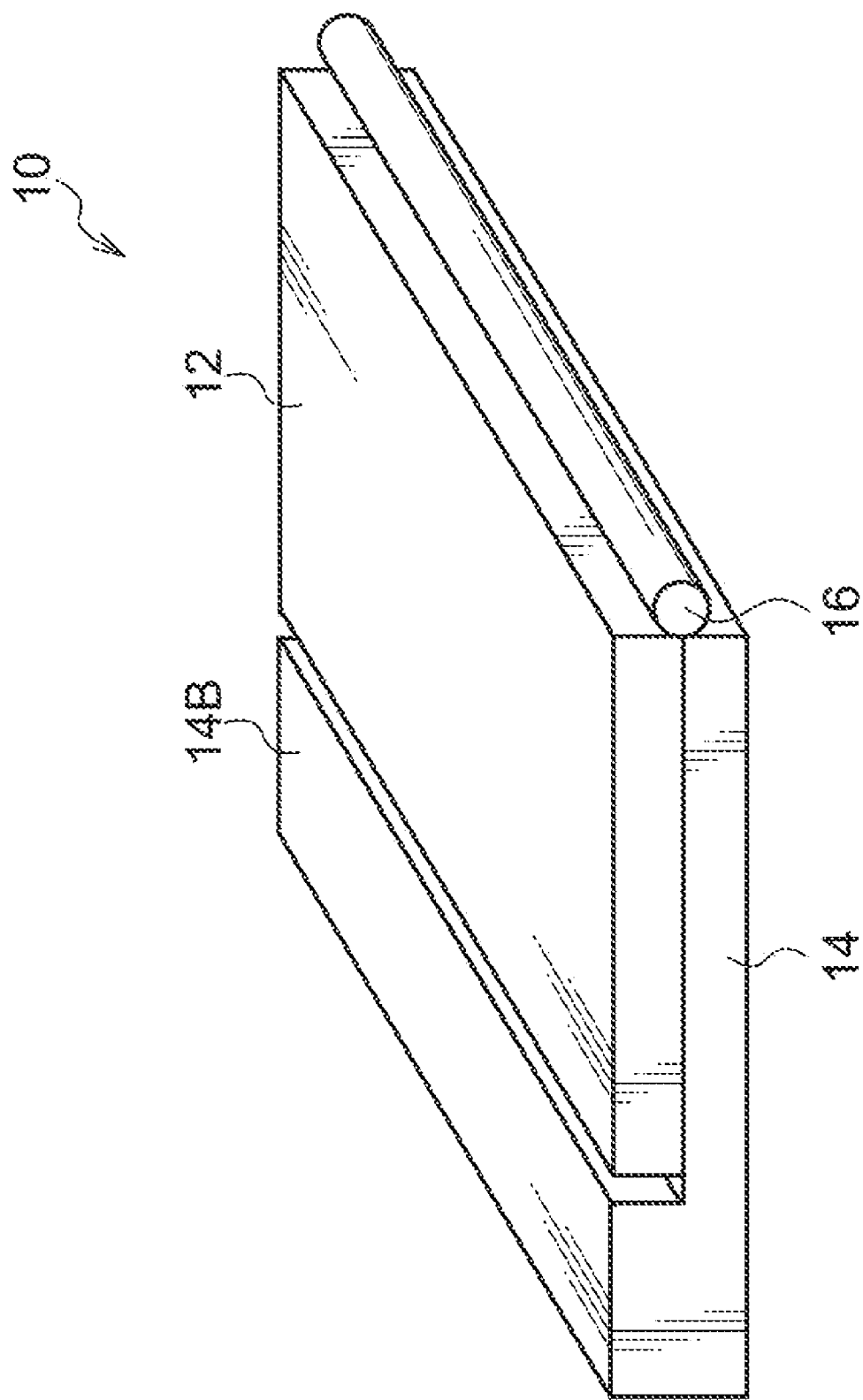
FIG. 15 is a perspective view showing the structure of the electronic cassette in the housed state relating to another exemplary embodiment.
Figure 16:
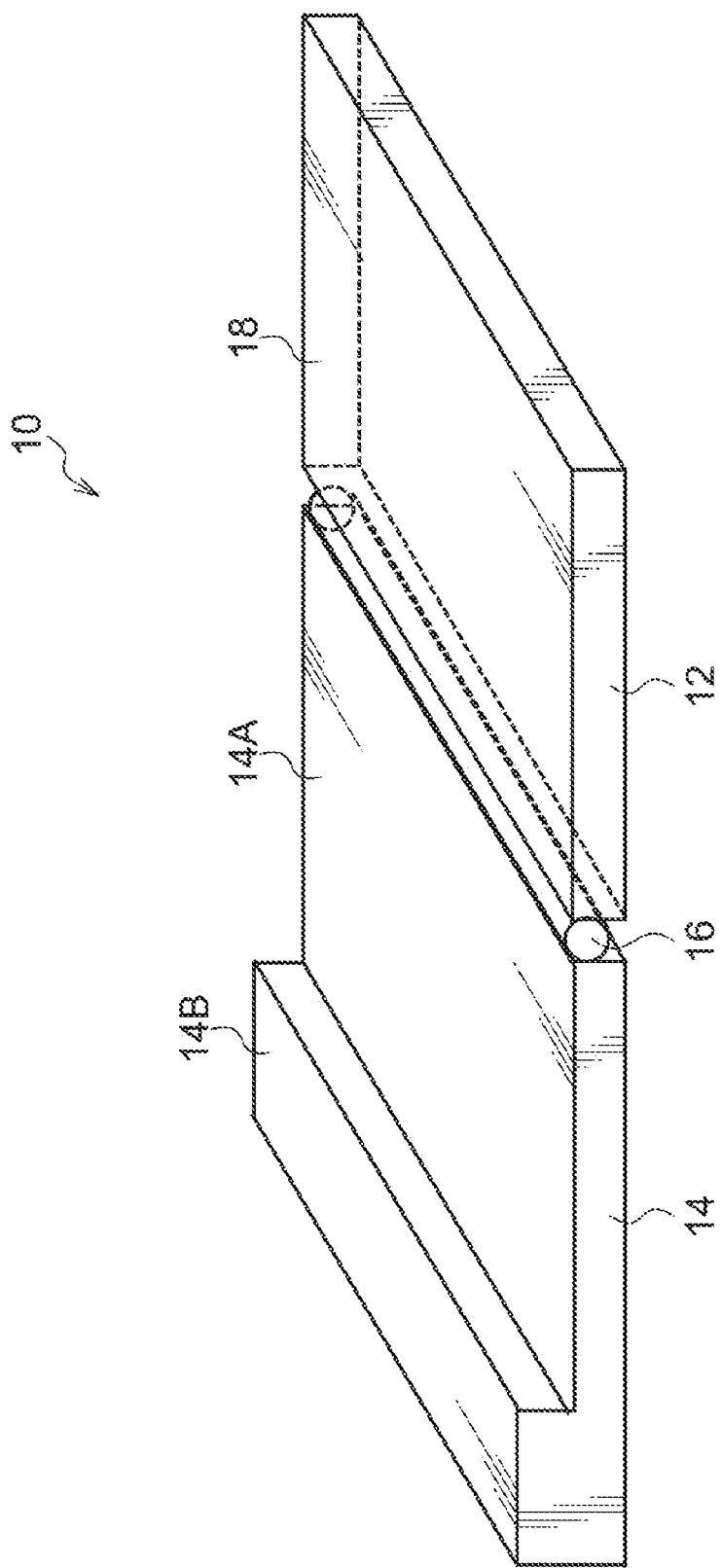
FIG. 16 is a perspective view showing the structure of the electronic cassette in the expanded state relating to another exemplary embodiment.

Note that the above first exemplary embodiment describes a case in which the image capturing unit 12 and the control unit 14 are formed to be the same height in order to eliminate a step between the image capturing unit 12 and the control unit 14 in the expanded state (FIG. 2). However, the present invention is not limited to the same. For example, in the same way as a liquid crystal display, the radiation detector 20 can be formed at a glass substrate and can be made to be relatively thin. On the other hand, at the controller 50, the circuits such as the inductors and the coils and the like are relatively thick, and, further, the battery and the like as well are relatively thick. Thus, as shown in FIG. 15 and FIG. 16, at the electronic cassette 10, the image capturing unit 12 may be formed to be thin, and the control unit 14 may be structured such that an overlapped portion 14A, on which the image capturing unit 12 is folded-up and superimposed in the housed state, is formed to be thin and the same thickness as the image capturing unit 12, and a non-overlapped portion 14B, on which the image capturing unit 12 is not superimposed, is formed to be thick, and circuits such as the inductors and coils and the like, and the battery, are disposed within the non-overlapped portion 14B. The display section 19A and the operation panel 19B may be provided at the overlapped portion 14A or may be provided at the non-overlapped portion 14B.

Further, the first and second exemplary embodiments describe cases in which radio communication with an external device such as the console or the like is carried out. However, the present invention is not limited to the same. For example, wired communication may be carried out. In this case as well, by providing a connector, to which is connected a cable for carrying out wired communication, at the control unit 14, the connector and the cable do not bother the patient. Further, when placing the cassette in under the subject, no frictional resistance or excessive load is applied, and it is therefore difficult for troubles with poor contact such as looseness or disconnection or the like to arise.

Although the first and second exemplary embodiments describe cases in which information relating to the patient is displayed on the display section 19A, the present invention is not limited to the same. For example, the captured radiographic image or the image capturing conditions may be displayed. Further, if the same region that is the object of image capturing of the patient is captured periodically and changes over time are observed, radiographic images that have been captured in the past at that region that is the object of image capturing of the patient may be received from the console and displayed. Moreover, a sample image or image capturing guidance may be displayed in accordance with the region that is the object of image capturing.

Figure 17:
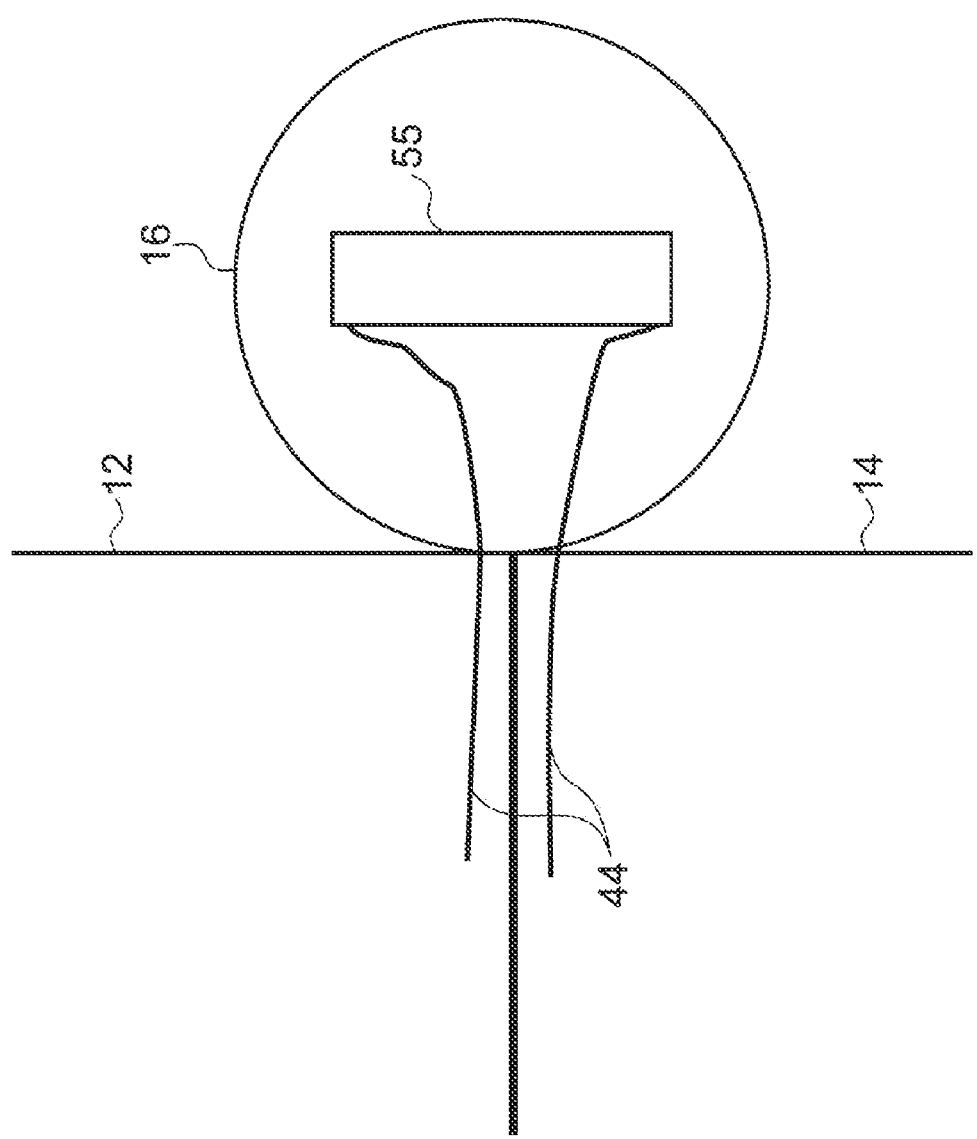
FIG. 17 is a sectional view showing a structure in which an integrated circuit is provided within a hinge relating to another exemplary embodiment.
Figure 18:
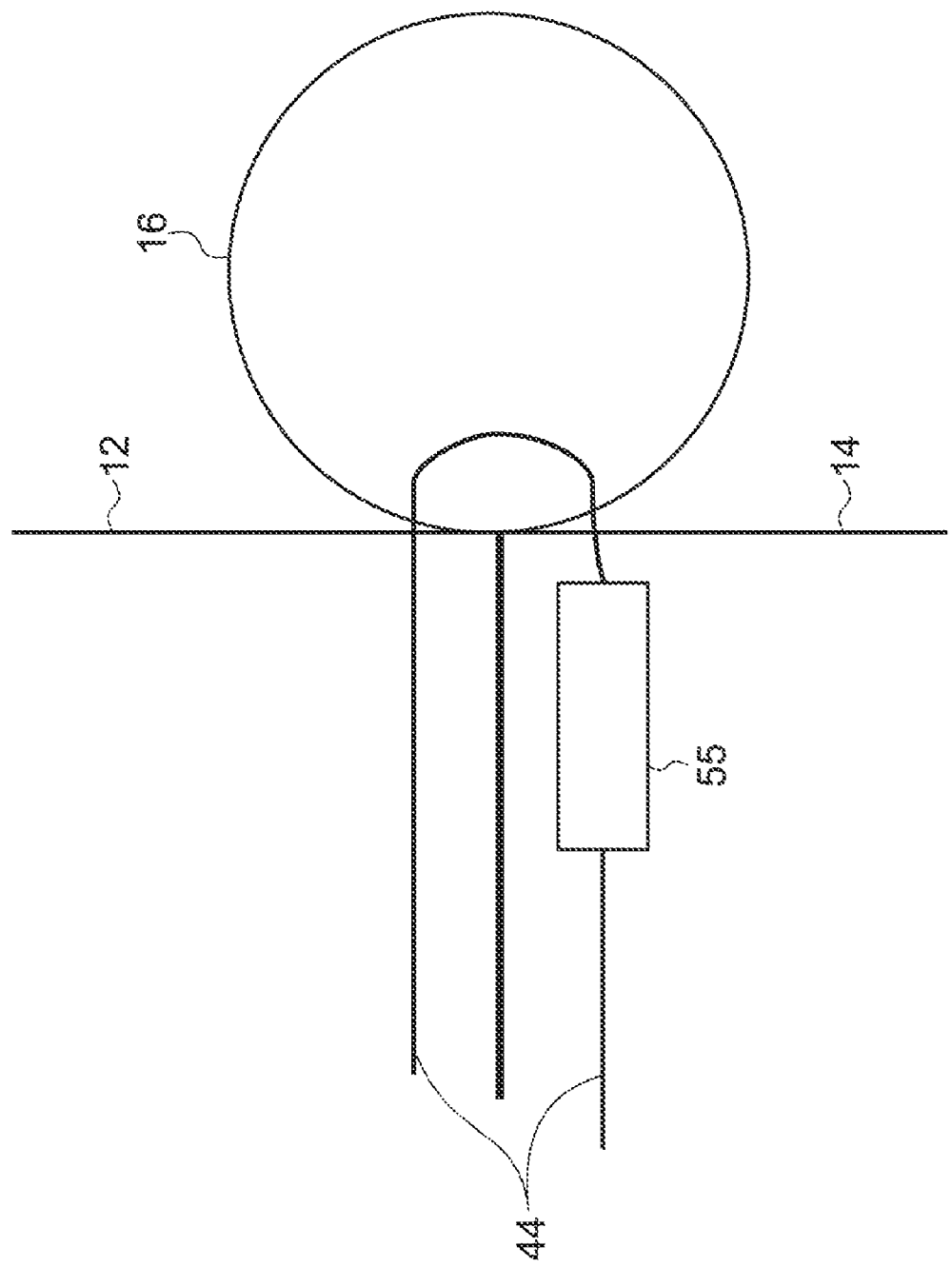
FIG. 18 is a sectional view showing a structure in which the integrated circuit is provided in a vicinity of the hinge relating to another exemplary embodiment.

The above first exemplary embodiment describes a case in which the gate line driver 52 and the signal processor 54 are provided within the control unit 14, but the present invention is not limited to the same. For example, the gate line driver 52 and/or the signal processor 54 may be structured by an integrated circuit 55 such as an ASIC (Application Specific Integrated Circuit) or the like, and may be disposed within the hinge 16 as shown in FIG. 17. Due thereto, the effect of cooling the integrated circuit 55 can be improved. Note that the integrated circuit 55 does not necessarily have to be provided within the hinge 16, and may be disposed in a vicinity of the hinge 16 as shown in FIG. 18.

Further, the above respective exemplary embodiments describe cases in which the present invention is applied to the indirect-conversion-type radiation detector 20 that once converts radiation into light at the scintillator layer 28, and converts the converted light into charges at the photoconductive layers 30 and accumulates the charges. However, the present invention is not limited to the same and may be applied to, for example, a direct-conversion-type radiation detector that directly converts radiation into charges at sensor portions using amorphous selenium or the like, and accumulates the charges.

In a direct-conversion-type radiation detector, as shown in FIG. 19, a photoconductive layer 48 that converts incident radiation into charges is formed, as an example of a radiation conversion layer that converts incident radiation, on the TFT substrate 26.

Compounds whose main component is at least one of amorphous Se, $Bi_{12}MO_{20}$ (M: Ti, Si, Ge), $Bi_4M_3O_{12}$ (M: Ti, Si, Ge), $Bi_2O_3$, $BiMO_4$ (M: Nb, Ta, V), $Bi_2WO_6$, $Bi_{24}B_2O_{39}$, ZnO, ZnS, ZnSe, ZnTe, $MNbO_3$ (M: Li, Na, K), PbO, $HgI_2$, $PbI_2$, CdS, CdSe, CdTe, $BiI_3$, GaAs or the like, are used as the photoconductive layer 48. Amorphous materials, that have high dark resistance, exhibit good photoconductivity with respect to X-ray irradiation, and at which large surface area growth at low temperatures by vacuum deposition is possible, are preferable.

A bias electrode 49, that is formed on the obverse side of the photoconductive layer 48 and is for applying bias voltage to the photoconductive layer 48, is formed on the photoconductive layer 48.

In the direct-conversion-type radiation detection device, in the same way as in the indirect-conversion-type radiation detection device, the charge collecting electrodes 34, that collect the charges generated at the photoconductive layer 48, are formed at the TFT substrate 26.

Further, the TFT substrate 26 in the direct-conversion-type radiation detection device has charge storage capacitors 35 that accumulate the charges collected at the respective charge collecting electrodes 34. The charges that are accumulated in the respective charge storage capacitors 35 are read-out by the switch elements 24.

Moreover, the structures of the electronic cassette 10 and the radiation detector 20 that were described in the above exemplary embodiments are examples, and appropriate changes may be made within a range that does not deviate from the gist of the present invention.

In the portable radiographic image capturing device of the present invention, a radiographic image, that is expressed by radiation irradiated onto the radiation surface, is captured by the image capturing unit at which is provided the radiation surface onto which radiation is irradiated at the time of capturing a radiographic image. The radiation detector, that outputs electric signals expressing the captured radiographic image, is incorporated in the image capturing unit. Radiographic images by radiation that is irradiated onto the radiation surface can be captured. Further, a controller, that controls the image capturing operations of the radiation detector, is incorporated in the control unit that is connected to the image capturing unit. The control unit can be changed between the expanded state in which the radiation surface is exposed to the exterior and the housed state in which the control unit covers the radiation surface.

In this way, in accordance with the present invention, the control unit, that incorporates therein the controller that controls the image capturing operations of the radiation detector, is connected, so as to be able to change between the expanded state in which the radiation surface is exposed to the exterior and the housed state in which the control unit covers the radiation surface, to the image capturing unit that incorporates the radiation detector therein and that captures radiographic images by radiation that is irradiated onto the radiation surface. Therefore, because the control unit can be set in the housed state in which the radiation surface is covered by the control unit, damage to the radiation surface when the portable radiographic image capturing device is carried around can be prevented. Further, the cooling effect can be improved by setting the image capturing unit and the control unit in the expanded state.

In the aspect of the present invention, the portable radiographic image capturing device may further have a connecting member that connects the image capturing unit and the control unit such that the control unit can be changed between an expanded state, in which the image capturing unit and the control unit are lined-up next to one another, and a housed state, in which the image capturing unit and the control unit are folded-up so as to be superimposed on one another, wherein the radiation surface is provided at a surface of the image capturing unit which surface faces the control unit in the housed state.

Further, in the aspect of the present invention, an accommodating portion, that can accommodate the image capturing unit therein, may be provided at the control unit, and the control unit may be able to be changed between a housed state, in which the image capturing unit is accommodated in the accommodating portion, and an expanded state, in which the image capturing unit is pulled-out from the accommodating portion.

Moreover, in the aspect of the present invention, an amplifying circuit, that amplifies the electric signals outputted from the radiation detector, may be provided within the connecting member.

In the aspect of the present invention, a radio communication section, that carries out radio communication with an external device, may be provided at the control unit.

Further, in the aspect of the present invention, a surface of the control unit may be formed to have convex and concave shapes.

Moreover, in the aspect of the present invention, the control unit may have a display section at a surface that opposes the image capturing unit in the housed state.

The radiographic image capturing device of the present invention has the effect of, while improving the cooling effect, being able to prevent the radiation surface from being damaged when the radiographic image capturing device is carried around.

The above respective exemplary embodiments describe cases in which the present invention is applied to a radiographic image capturing device that captures radiographic images by detecting X-rays as radiation. However, the present invention is not limited to the same. The radiation that is the object of detection may be, other than X-rays, any of gamma rays, a particle beam or the like for example.

What is claimed is:

1. A portable radiographic image capturing device comprising:
    an image capturing unit at which is provided a radiation surface that is irradiated at a time of capturing a radiographic image, and that captures a radiographic image expressed by radiation irradiated onto the radiation surface, and that incorporates therein a radiation detector that outputs electric signals expressing the captured radiographic image; and a control unit that is connected to the image capturing unit, and that incorporates therein a controller that controls image capturing operations of the radiation detector, and that can be changed between an expanded state in which the radiation surface is exposed to an exterior and a housed state in which the control unit covers the radiation surface.

2. The portable radiographic image capturing device of claim 1, further comprising a connecting member that connects the image capturing unit and the control unit such that the control unit can be changed between an expanded state, in which the image capturing unit and the control unit are lined-up next to one another, and a housed state, in which the image capturing unit and the control unit are folded-up so as to be superimposed on one another, wherein the radiation surface is provided at a surface of the image capturing unit which surface faces the control unit in the housed state.

3. The portable radiographic image capturing device of claim 2, wherein an amplifying circuit, that amplifies the electric signals outputted from the radiation detector, is provided within the connecting member.

4. The portable radiographic image capturing device of claim 3, wherein a radio communication section, that carries out radio communication with an external device, is provided at the control unit.

5. The portable radiographic image capturing device of claim 3, wherein a surface of the control unit is formed to have convex and concave shapes.

6. The portable radiographic image capturing device of claim 3, wherein the control unit has a display section at a surface that opposes the image capturing unit in the housed state.

7. The portable radiographic image capturing device of claim 2, wherein a radio communication section, that carries out radio communication with an external device, is provided at the control unit.

8. The portable radiographic image capturing device of claim 2, wherein a surface of the control unit is formed to have convex and concave shapes.

9. The portable radiographic image capturing device of claim 2, wherein the control unit has a display section at a surface that opposes the image capturing unit in the housed state.

10. The portable radiographic image capturing device of claim 1, wherein an accommodating portion, that can accommodate the image capturing unit, is provided at the control unit, and the control unit can be changed between a housed state, in which the image capturing unit is accommodated in the accommodating portion, and an expanded state, in which the image capturing unit is pulled-out from the accommodating portion.

11. The portable radiographic image capturing device of claim 10, wherein a radio communication section, that carries out radio communication with an external device, is provided at the control unit.

12. The portable radiographic image capturing device of claim 10, wherein a surface of the control unit is formed to have convex and concave shapes.

13. The portable radiographic image capturing device of claim 10, wherein the control unit has a display section at a surface that opposes the image capturing unit in the housed state.

14. The portable radiographic image capturing device of claim 1, wherein a radio communication section, that carries out radio communication with an external device, is provided at the control unit.

15. The portable radiographic image capturing device of claim 1, wherein a surface of the control unit is formed to have convex and concave shapes.

16. The portable radiographic image capturing device of claim 1, wherein the control unit has a display section at a surface that opposes the image capturing unit in the housed state.

17. The portable radiographic image capturing device of claim 1, wherein the radiation detector is formed at a substrate that is structured to contain plastic resin, aramid, bio-nanofibers, or flexible glass.

18. The portable radiographic image capturing device of claim 1, wherein a conversion layer, that converts radiation irradiated onto a substrate into light, and a plurality of sensor portions, at which charges are generated due to light that was converted at the conversion layer being irradiated, are formed at the radiation detector, and the radiation detector is incorporated in the image capturing unit such that radiation that is irradiated onto the irradiated surface is incident from the substrate side.

19. The portable radiographic image capturing device of claim 18, wherein the sensor portions are structured to contain an organic photoelectric conversion material.

20. The portable radiographic image capturing device according to claim 1, wherein the control unit and the image capturing unit are configured to rotate about a common axis of a single hinge included in the connecting member.

* * * * *